(12) United States Patent
Hochman

(10) Patent No.: US 11,141,113 B2
(45) Date of Patent: Oct. 12, 2021

(54) DETECTION OF HUMAN-MACHINE INTERACTION ERRORS

(71) Applicants: Eldad Izhak Hochman, Raanana (IL); Zvi Ginosar, Mevasseret Zion (IL)

(72) Inventor: Eldad Izhak Hochman, Raanana (IL)

(73) Assignees: Eldad Izhak Hochman, Raanana (IL); Zvi Ginosar, Mevasseret Zion (IL)

(*) Notice: Subject to any disclaimer, the term of this patent is extended or adjusted under 35 U.S.C. 154(b) by 113 days.

(21) Appl. No.: 16/566,056

(22) Filed: Sep. 10, 2019

(65) Prior Publication Data
US 2020/0000409 A1 Jan. 2, 2020

Related U.S. Application Data

(63) Continuation of application No. 15/321,619, filed as application No. PCT/IL2015/050633 on Jun. 22, 2015, now Pat. No. 10,413,246.

(Continued)

(51) Int. Cl.
*A61B 5/00* (2006.01)
*A61B 5/0488* (2006.01)
(Continued)

(52) U.S. Cl.
CPC ............ *A61B 5/6897* (2013.01); *A61B 3/113* (2013.01); *A61B 3/1241* (2013.01); *A61B 5/11* (2013.01);
(Continued)

(58) Field of Classification Search
CPC ......... A61B 5/6897; A61B 5/24; A61B 5/369; A61B 5/389; A61B 5/163; A61B 3/113; A61B 3/1241; A61B 5/16; A61B 5/4803; A61B 5/11; A61B 5/225; G09B 5/00; G06F 3/015; G06F 3/167; G06F 3/012;
(Continued)

(56) References Cited

U.S. PATENT DOCUMENTS 8,581,870 B2 11/2013 Bokma et al.
2006/0101079 A1 5/2006 Morikawa et al.
(Continued)

FOREIGN PATENT DOCUMENTS

WO 2012061707 A2 5/2012
WO 2013085580 A1 6/2013

OTHER PUBLICATIONS

Kreilinger, A., et al., "Detection of error potentials during a car-game with combined continuous and discrete feedback". Conference paper, 5th International Brain-Computer Interface meeting, Jun. 2013.
(Continued)

*Primary Examiner* — Cuong B Nguyen
(74) *Attorney, Agent, or Firm* — Kenealy Vaidya LLP

(57) ABSTRACT

Disclosed are a system and method of detection of an interaction-error. The interaction-error is derived from an incorrect decision and is directed to interacting with a machine. During human-machine interaction, command related data values are obtained. Command related data values characterize any one of an interacting-command and an interacting-action. The command related data values are compared with command related reference data values, and an interaction-error is identified if a difference between the command related data values and the command related reference data values complies with a predefined criterion.

21 Claims, 7 Drawing Sheets

Related U.S. Application Data

(60) Provisional application No. 62/015,715, filed on Jun. 23, 2014.

(51) Int. Cl.

| | |
|---|---|
| A61B 5/11 | (2006.01) |
| A61B 5/22 | (2006.01) |
| G06F 3/01 | (2006.01) |
| G06F 11/34 | (2006.01) |
| A61B 5/24 | (2021.01) |
| A61B 5/369 | (2021.01) |
| A61B 5/389 | (2021.01) |
| A61B 3/113 | (2006.01) |
| A61B 3/12 | (2006.01) |
| A61B 5/16 | (2006.01) |
| G06F 3/16 | (2006.01) |
| G09B 5/00 | (2006.01) |
| G06F 11/00 | (2006.01) |
| G06F 11/07 | (2006.01) |

(52) U.S. Cl.
CPC ............... *A61B 5/16* (2013.01); *A61B 5/225* (2013.01); *A61B 5/24* (2021.01); *A61B 5/369* (2021.01); *A61B 5/389* (2021.01); *A61B 5/4803* (2013.01); *G06F 3/012* (2013.01); *G06F 3/013* (2013.01); *G06F 3/015* (2013.01); *G06F 3/167* (2013.01); *G06F 11/3438* (2013.01); *G09B 5/00* (2013.01); *A61B 5/163* (2017.08); *G06F 11/004* (2013.01); *G06F 11/0796* (2013.01); *G06F 2203/011* (2013.01)

(58) Field of Classification Search
CPC .... G06F 3/013; G06F 11/3438; G06F 11/004; G06F 11/0796; G06F 2203/011
See application file for complete search history.

(56) References Cited

U.S. PATENT DOCUMENTS

| | | | |
|---|---|---|---|
| 2007/0266273 | A1 | 11/2007 | Adachi et al. |
| 2010/0106042 | A1 | 4/2010 | Morikawa et al. |
| 2013/0141342 | A1 | 6/2013 | Bokma et al. |
| 2013/0228023 | A1 | 9/2013 | Drasnin et al. |
| 2014/0035856 | A1 | 2/2014 | Bokma et al. |
| 2015/0161998 | A1 | 6/2015 | Park et al. |
| 2016/0256068 | A1 | 9/2016 | Harrison |

OTHER PUBLICATIONS

Van Boxtel, G. J., et al., "Differential involvement of the anterior cingulate cortex in performance monitoring during a stop-signal task". Journal of Psychophysiology, (2005), 19(1), 1-10.

Dikman, Z. V., et al., "Error monitoring during reward and avoidance learning in high-and low-socialized individuals". Psychophysiology, (2000), 37(01), 43-54.

Navarro-Cebrian, A., et al., Error-monitoring and post-error compensations: "dissociation between perceptual failures and motor errors with and without awareness". Journal of Neuroscience, (2013), 33(30), 12375-12383.

Zhang, H., et al., "Improved recognition of error related potentials through the use of brain connectivity features". In Engineering in Medicine and Biology Society (EMBC), (Aug. 2012), 2012 Annual International Conference of the IEEE (pp. 6740-6743). IEEE.

Endrass, T., et al., "Error awareness in a saccade countermanding task". Journal of Psychophysiology, (2005), 19(4), 275.

Endrass, T., et al., "Overactive performance monitoring in obsessive-compulsive disorder: ERP evidence from correct and erroneous reactions". Neuropsychologia, (2008), 46(7), 1877-1887.

Endrass, T., et al., "Speeding up older adults: age-effects on error processing in speed and accuracy conditions". Biological Psychology, (2012), 89(2), 426-432.

Endrass, T., et al., "ERP correlates of conscious error recognition: aware and unaware errors in an antisaccade task". European Journal of Neuroscience, (2007), 26(6), 1714-1720.

Inzlicht, M., et al., "ERN and the placebo: A misattribution approach to studying the arousal properties of the error-related negativity". Journal of Experimental Psychology: General, (2012), 141(4), 799.

Falkenstein, M., et al., "Effects of crossmodal divided attention on late ERP components. II. Error processing in choice reaction tasks". Electroencephalography and Clinical Neurophysiology, (1991), 78(6), 447-455.

Falkenstein, M., et al., "ERP components on reaction errors and their functional significance: a tutorial". Biological psychology, (2000), 51(2), 87-107.

Ferrez, P. W., et al., "Error-related EEG potentials generated during simulated brain—computer interaction". IEEE transactions on biomedical engineering, (2008), 55(3), 923-929.

Fiehler, K., et al., "Electrophysiological correlates of error correction". Psychophysiology, (2005), 42(1), 72-82.

Wessel, J. R., "Error awareness and the error-related negativity: evaluating the first decade of evidence". Frontiers in Human Neuroscience, (2012), 6, 88.

Van Steenbergen, H., et al., "Pupil dilation in the Simon task as a marker of conflict processing". Frontiers in Human Neuroscience, (2013), 7, 215.

Maidhof, C., et al., "Predictive error detection in pianists: a combined ERP and motion capture study". Frontiers in Human Neuroscience, (2013), 7, 587.

Frank, M. J., et al., "Error-related negativity predicts reinforcement learning and conflict biases". Neuron, (2005), 47(4), 495-501.

Gehring, W. J., et al., "A brain potential manifestation of error-related processing". Electroencephalography and Clinical Neurophysiology—Supplements only, (1995), 44, 261-272.

Gehring, W. J., et al., "A neural system for error detection and compensation". Psychological Science, (1993), 4(6), 385-390.

Hajcak, G., "What we've learned from mistakes: Insights from error-related brain activity". Current Directions in Psychological Science, (2012), 21(2), 101-106.

Hoffmann, S., et al., "Predictive information processing in the brain: errors and response monitoring". International Journal of Psychophysiology, (2012), 83(2), 208-212.

Holdroyd, C. B., et al., "The neural basis of human error processing: reinforcement learning, dopamine, and the error-related negativity". Psychological Review, (2002), 109(4), 679.

Kreilinger, A., et al., "Implementation of error detection into the graz-brain-computer interface, the interaction error potential". In AAATE'09: 9th European Conf. for the Advancement of Assistive Technology (2009), (Florence, Italy) (pp. 1-5).

Iturrate, I., et al., "Robot reinforcement learning using EEG-based reward signals". In Robotics and Automation (ICRA), (May 2010), 2010 IEEE International Conference on (pp. 4822-4829). IEEE.

Iturrate, I., et al., "Latency correction of error potentials between different experiments reduces calibration time for single-trial classification". In Engineering in Medicine and Biology Society (EMBC), (Aug. 2012), 2012 Annual International Conference of the IEEE (pp. 3288-3291). IEEE.

Iturrate, I., et al.,"Task-dependent signal variations in EEG error-related potentials for brain-computer interfaces". Journal of Neural Engineering, (2013), 10(2), 026024.

Kopp, B., et al., "An event-related brain potential substrate of disturbed response monitoring in paranoid schizophrenic patients". Journal of Abnormal Psychology, (1999), 108(2), 337.

Maidhof, C., et al., "Nobody is perfect: ERP effects prior to performance errors in musicians indicate fast monitoring processes". PLoS One, (2009), 4(4), e5032.

Milekovic, T., et al., "Detection of error related neuronal responses recorded by electrocorticography in humans during continuous movements". PLoS one, (2013), 8(2), e55235.

Lindström, B. R., et al., "In your face: risk of punishment enhances cognitive control and error-related activity in the corrugator supercilii muscle". PLOS one, (2013), 8(6), e65692.

(56) References Cited

OTHER PUBLICATIONS

Fiehler, K., et al., "Cardiac responses to error processing and response conflict". Errors, conflicts, and the brain. Current opinions on performance monitoring. MPI for Human Cognitive and Brain Sciences, Leipzig, (2004), 135-140.

Kim, S. K., et al., "Classifier transferability in the detection of error related potentials from observation to interaction". InSystems, Man, and Cybernetics (SMC), (Oct. 2013), 2013 IEEE International Conference on (pp. 3360-3365). IEEE.

Kobam, L., et al., "Brain systems underlying the affective and social monitoring of actions: an integrative review". Neuroscience & Biobehavioral Reviews, (2014), 46, 71-84.

Koelewijn, T., et al., "Motor-cortical beta oscillations are modulated by correctness of observed action". Neuroimage, (2008), 40(2), 767-775.

Kreilinger, A., et al., "Error potential detection during continuous movement of an artificial arm controlled by brain-computer interface". Medical & biological engineering & computing, (2012), 50(3), 223-230.

Lopez-Larraz, E., et al., "Real-time recognition of feedback error-related potentials during a time-estimation task". In Engineering in Medicine and Biology Society (EMBC), (Aug. 2010), 2010 Annual International Conference of the IEEE (pp. 2670-2673). IEEE.

López-Larraz, E., et al., EEG single-trial classification of visual, auditive and vibratory feedback potentials in Brain-Computer Interfaces. In Engineering in Medicine and Biology Society, EMBC, (Aug. 2011), 2011 Annual International Conference of the IEEE (pp. 4231-4234). IEEE.

Phlypo, R., et al., "A non-orthogonal SVD-based decomposition for phase invariant error-related potential estimation". In Engineering in Medicine and Biology Society, EMBC, (Aug. 2011), 2011 Annual International Conference of the IEEE (pp. 6963-6966). IEEE.

Mars, R. B., et al., "What if I told you:"You were wrong"? Brain potentials and behavioral adjustments elicited by feedback in a time-estimation task". Errors, conflicts, and the brain. Current opinions on performance monitoring, (2004), 129-134.

Masaki, H., et al., "Does the error negativity reflect response conflict strength? Evidence from a Simon task". Psychophysiology, (2007), 44(4), 579-585.

Sandra, R., et al., "Designing spatial filters based on neuroscience theories to improve error-related potential classification". In Machine Learning for Signal Processing (MLSP), (Sep. 2012), 2012 IEEE International Norkshop on (pp. 1-6). IEEE.

Taylor, S. F., et al., "Neural systems for error monitoring recent findings and theoretical perspectives". The Neuroscientist,(2007), 13(2), 160-172.

Nieuwenhuis, S., et al., "Error-related brain potentials are differentially related to awareness of response errors: Evidence from an antisaccade task". Psychophysiology, (2001), 38(5), 752-760.

Olvet, D. M., et al., "The error-related negativity (ERN) and psychopathology: toward an endophenotype". Clinical Psychology Review, (2008), 28(8), 1343-1354.

Weinberg, A., et al., "Increased error-related brain activity distinguishes generalized anxiety disorder with and without comorbid major depressive disorder". Journal of Abnormal Psychology, (2012), 121(4), 885.

Van Schie, H. T., et al., "Modulation of activity in medial frontal and motor cortices during error observation". Nature Neuroscience, (2004), 7(5), 549-554.

Omedes, J., et al., "Using frequency-domain features for the generalization of EEG error-related potentials among different tasks". In Engineering in Medicine and Biology Society (EMBC), (Jul. 2013), 2013 35th Annual International Conference of the IEEE (pp. 5263-5266). IEEE.

Yordanova, J., et al., "Parallel systems of error processing in the brain". Neuroimage, (2004), 22(2), 590-602.

Putze, F., et al., "Reliable subject-adapted recognition of EEG error potentials using limited calibration data". In Neural Engineering (NER), (Nov. 2013), 2013 6th International IEEE/EMBS Conference on(pp. 419-422). IEEE.

International Search Report and Written Opinion issued in PCT/IL2015/050633 dated Oct. 25, 2015.

Aron, A. R., et al. "Stop-signal inhibition disrupted by damage to right inferior frontal gyrus in humans." Nature Neuroscience 6.2 (2003): 115-116.

Eriksen, B. A., et al., "Effects of noise letters upon the identification of a target letter in a nonsearch task." Attention, Perception, & Psychophysics 16.1 (1974): 143-149.

Konishi S., et al. "No-go dominant brain activity in human inferior prefrontal cortex revealed by functional magnetic resonance imaging."European Journal of Neuroscience 10.3 (1998): abstract.

Logan, G. D., et al. "On the ability to inhibit thought and action: A theory of an act of control." Psychological review 91.3 (1984): 295.

Rorden, C., et al., "An evaluation of traditional and novel tools for lesion behavior mapping." Neuroimage 44.4 (2009): 1355-1362.

https://www.stuff.tv/news/hands-amazing-pressure-sensitive-keyboard-and-music-kit-are-best-things-about-microsoft-surface . (Oct. 13, 2013).

Holroyd, C. B., et al."Errors in reward prediction are reflected in the event-related brain potential". Neuroreport (2003), 14(18), 2481-2484.

Critchley, H. D. "Psychophysiology of neural, cognitive and affective integration: fMRI and autonomic indicants". International Journal of Psychophysiology, (2009) 73(2), 88-94.

Holroyd, C. B., et al., "Error-related scalp potentials elicited by hand and foot movements: evidence for an output-independent error-processing system in humans". Neuroscience Letters, (1998) 242(2), 65-68.

Hajcak, G., et al. "On the ERN and the significance of errors". Psychophysiology, (2005), 42(2), 151-160.

Llera A. et al., "On the use of interaction error potentials for adaptive brain computer interfaces". Neural Networks, (2011), 24(10), 1120-1127.

Allain, S., et al., "The modulation of the Ne-like wave on correct responses foreshadows errors".Neuroscience Letters, (2004), 372(1), 161-166.

Spüler, M., et al., "Online use of error-related potentials in healthy users and people with severe motor impairment increases performance of a P300-BCI". Clinical Neurophysiology, (2012), 123(7), 1328-1337.

Zhang, H., et al., "Inferring driver's turning direction through detection of error related brain activity". In Engineering in Medicine and Biology Society (EMBC), (Jul. 2013), 2013 35th Annual International Conference of the IEEE (pp. 2196-2199). IEEE.

Dal Seno, B., et al., "Online detection of P300 and error potentials in a BCI speller". Computational intelligence and Neuroscience, 2010, 11.

Ullsperger M., et al., "Neurophysiology of performance monitoring and adaptive behavior". Physiological reviews, (2014), 94(1), 35-79.

Wessel, J. R., et al., "Saccade suppression exerts global effects on the motor system". Journal of Neurophysiology, (2013), 110(4), 883-890.

Coles, M. G., et al., "Why is there an ERN/Ne on correct trials? Response representations, stimulus-related components, and the theory of error-processing". Biological Psychology, (2001), 56(3), 173-189.

Holroyd, C. B., et al., "Spared error-related potentials in mild to moderate Parkinson's disease".Neuropsychologia, (2002), 40(12), 2116-2124.

Wessel, J. R., et al., "Unexpected events induce motor slowing via a brain mechanism for action-stopping with global suppressive effects". Journal of Neuroscience, (2013), 33(47), 18481-18491.

Olvet, D. M., et al., "The stability of error-related brain activity with increasing trials". Psychophysiology, (2009), 46(5), 957-961.

Schalk, G., et al., "EEG-based communication: presence of an error potential". Clinical Neurophysiology, (2000), 111(12), 2138-2144.

Rodríguez-Fornells, A., et al., "Time course of error detection and correction in humans: neurophysiological evidence".Journal of Neuroscience, (2002), 22(22), 9990-9996.

Wessel, J. R., et al., "Error awareness revisited: accumulation of multimodal evidence from central and autonomic nervous systems". Journal of Cognitive Neuroscience, (2011), 23(10), 3021-3036.

(56) References Cited

OTHER PUBLICATIONS

Houk, J. C., et al., "Action selection and refinement in subcortical loops through basal ganglia and cerebellum". Philosophical Transactions of the Royal Society of London B: Biological Sciences, (2007), 362(1485), 1573-1583.
Margaux, P., et al., "Objective and subjective evaluation of online error correction during P300-based spelling". Advances in Human-Computer Interaction, (2012), 2012, 4.
Hajcak, G., et al., "Errors are aversive: Defensive motivation and the error-related negativity". Psychological Science, (2008), 19(2), 103-108.
Mühl, C., et al., (2009). ACII 2009: Affective Computing & Intelligent Interaction: Proceedings vol. II.
Ullsperger, M., et al., "Conscious perception of errors and its relation to the anterior insula". Brain Structure and Function, (2010), 214(5-6), 629-643.
Schmidt, N. M., et al., "Online detection of error-related potentials boosts the performance of mental typewriters". BMC Neuroscience, (2012), 13(1), 19.
Artusi, X., et al., "Performance of a simulated adaptive BCI based on experimental classification of movement-related and error potentials". IEEE Journal on Emerging and Selected Topics in Circuits and Systems, (2011), 1(4), 480-488.
Tsoneva, T., et al., "Towards error-free interaction". In Engineering in Medicine and Biology Society (EMBC), (Aug. 2010), 2010 Annual International Conference of the IEEE (pp. 5799-5802). IEEE.
Blankertz, B., et al., "Boosting bit rates and error detection for the classification of fast-paced motor commands based on single-trial EEG analysis". IEEE Transactions on Neural Systems and Rehabilitation Engineering, (2003), 11(2), 127-131.
Bollon, J. M., et al., "EEG error-related potentials detection with a Bayesian filter". In Neural Engineering, (Apr. 2009), 2009. NER'09. 4th International IEEE/EMBS Conference on(pp.702-705). IEEE.
Brázdil, M., et al., "Error processing—evidence from intracerebral ERP recordings".Experimental Brain Research, (2002), 146(4), 460-466.
Burle, B., et al., "Error negativity does not reflect conflict: a reappraisal of conflict monitoring and anterior cingulate cortex activity". Journal of Cognitive Neuroscience, (2008), 20(9), 1637-1655.
Burle, B. et al., Sequential compatibility effects and cognitive control: does conflict really matter?.Journal of Experimental Psychology: Human Perception and Performance,(2005), 31(4), 831.
Cacioppo, J. T., et al., "Electromyographic activity over facial muscle regions can differentiate the valence and intensity of affective reactions". Journal of personality and social psychology, (1986), 50(2), 260.
Carbonnell, L., et al., "Does the error negativity reflect the degree of response conflict?". Brain Research, (2006), 1095(1), 124-130.
Cavanagh, J. F., et al., "Prelude to and resolution of an error: EEG phase synchrony reveals cognitive control dynamics during action monitoring". Journal of Neuroscience, (2009), 29(1), 98-105.
Cavanagh, J. F., et al., "Theta lingua franca: A common mid-frontal substrate for action monitoring", Processes. Psychophysiology, (2012), 49(2), 220-238.
Chavarriaga, R., et al., "Learning from EEG error-related potentials in noninvasive brain-computer interfaces". IEEE transactions on neural systems and rehabilitation engineering, (2010), 18(4), 381-388.
Chavarriaga, R., et al., "Adaptation of hybrid human-computer interaction systems using EEG error-related potentials". In Engineering in Medicine and Biology Society (EMBC), (Aug. 2010), 2010 Annual International Conference of the IEEE(pp. 4226-4229). IEEE.
Chavarriage, R., et al., "Anticipation-and error-related EEG signals during realistic human-machine interaction: A study on visual and tactile feedback." In Engineering in Medicine and Biology Society (EMBC), (Aug. 2012), 2012 Annual International Conference of the IEEE (pp. 6723-6726). Ieee.

Coles, M. G., et al., "Where did you go wrong? Errors, partial errors, and the nature of human information processing". Acta Psychologica, (1995), 90(1), 129-144.
Combaz, A., et al., "Towards the detection of error-related potentials and its integration in the context of a P300 speller brain-computer interface" .Neurocomputing, (2012), 80, 73-82.
De Bruijn, E. R., et al., "Action monitoring in motor control: ERPs following selection and execution errors in a force production task". Psychophysiology, (2003), 40(5), 786-795.
Hajcak, G., et al., "Error-related psychophysiology and negative affect". Brain and Cognition, (2004), 56(2), 189-197.
Schalk, Gerwin, et al., "BCI2000: A General-Purpose Brain-Computer Interface (BCI) System," IEEE Transactions on Biomedical Engineering, vol. 51, No. 6, Jun. 2004, pp. 1034-1043.
Critchley, H. D., et al., "Anterior cingulate activity during error and autonomic response". Neuroimage, (2005), 27(4), 885-895.
Takahashi, H., et al., "Reliability-based automatic repeat request with error potential-based error correction for mproving P300 speller performance". Neural Information Processing. Models and Applications, (2010), 50-57.
Parra, L. C., et al., "Response error correction—a demonstration of improved human-machine performance using real-time EEG monitoring". (2003), IEEE transactions on neural systems and rehabilitation engineering, 11(2), 173-177.
Riesel, A., et al., "The ERN is the ERN is the ERN? Convergent validity of error-related brain activity across different tasks". Biological Psychology, (2013), 93(3), 377-385.
Scheffers, M. K., et al., "Performance monitoring in a confusing world: error-related brain activity, judgments of response accuracy, and types of errors". Journal of Experimental Psychology: Human Perception and Performance, (2000), 26(1), 141.
Gehring, W. J., et al., "Slamming on the brakes: An electrophysiological study of error response inhibition". In Poster presented at the annual meeting of the Cognitive Neuroscience Society, Washington, DC, (Apr. 1999).
Herrmann, M. J., et al., "Source localization (LORETA) of the error-related-negativity (ERN/Ne) and positivity (Pe)". Cognitive Brain Research, (2004), 20(2), 294-299.
Ullsperger, M., et al., "Subprocesses of performance monitoring: a dissociation of error processing and response competition revealed by event-related fMRI and ERPs". Neuroimage, (2001), 14(6), 1387-1401.
Themanson, J. R., et al., "Alterations in error-related brain activity and post-error behavior over time". Brain and Cognition, (2012), 80(2), 257-265.
Hajcak, G., et al., "To err is autonomic: Error-related brain potentials, ANS activity, and post-error compensatory behavior". Psychophysiology, (2003), 40(6), 895-903.
Trujillo, L. T., et al., "Theta EEG dynamics of the error-related negativity". Clinical Neurophysiology, (2007), 118(3), 645-668.
Tunik, E., et al., "Basal ganglia contribution to the initiation of corrective submovements". Neuroimage, (2009), 47(4), 1757-1766.
Ventouras, E M., et al., "Classification of error-related negativity (ERN) and positivity (Pe) potentials using kNN and support vector machines". Computers in Biology and Medicine, (2011), 41(2), 98-109.
Wang, S., et al., "Early detection of numerical typing errors using data mining techniques". IEEE Transactions on Systems, Man, and Cybernetics—Part A: Systems and Humans, (2011), 41(6), 1199-1212.
Tops, M., et al., "Task engagement and the relationships between the error-related negativity, agreeableness, behavioral shame proneness and cortisol" Psychoneuroendocrinology, (2006), 31(7), 847-858.
Willemssen, R., et al., "Error processing in patients with Parkinson's disease: the influence of medication state". Journal of Neural Transmission, (2008), 115(3), 461-468.
Hajcak, G., et al., "Anxiety and error-related brain activity". Biological Psychology, (2003), 64(1), 77-90.
Yeung, N., et al., "ERP correlates of feedback and reward processing in the presence and absence of response choice". Cerebral Cortex, (2004), 15(5), 535-544.

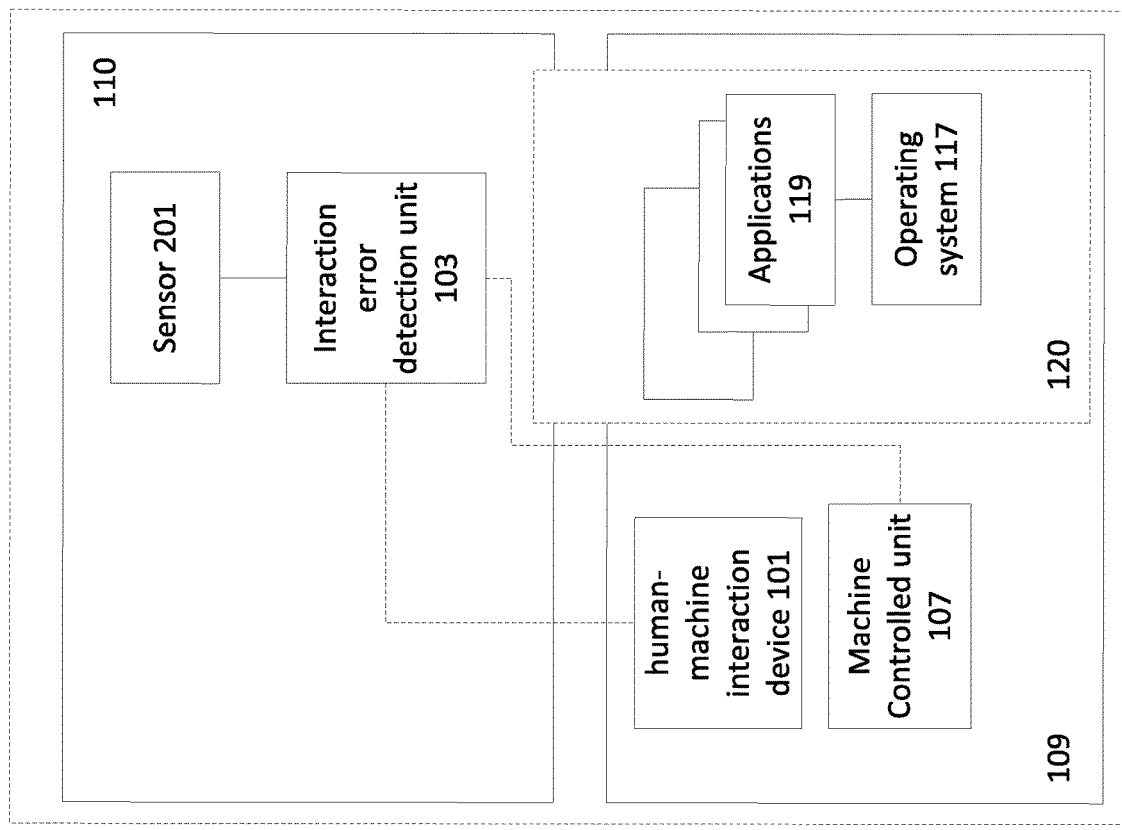
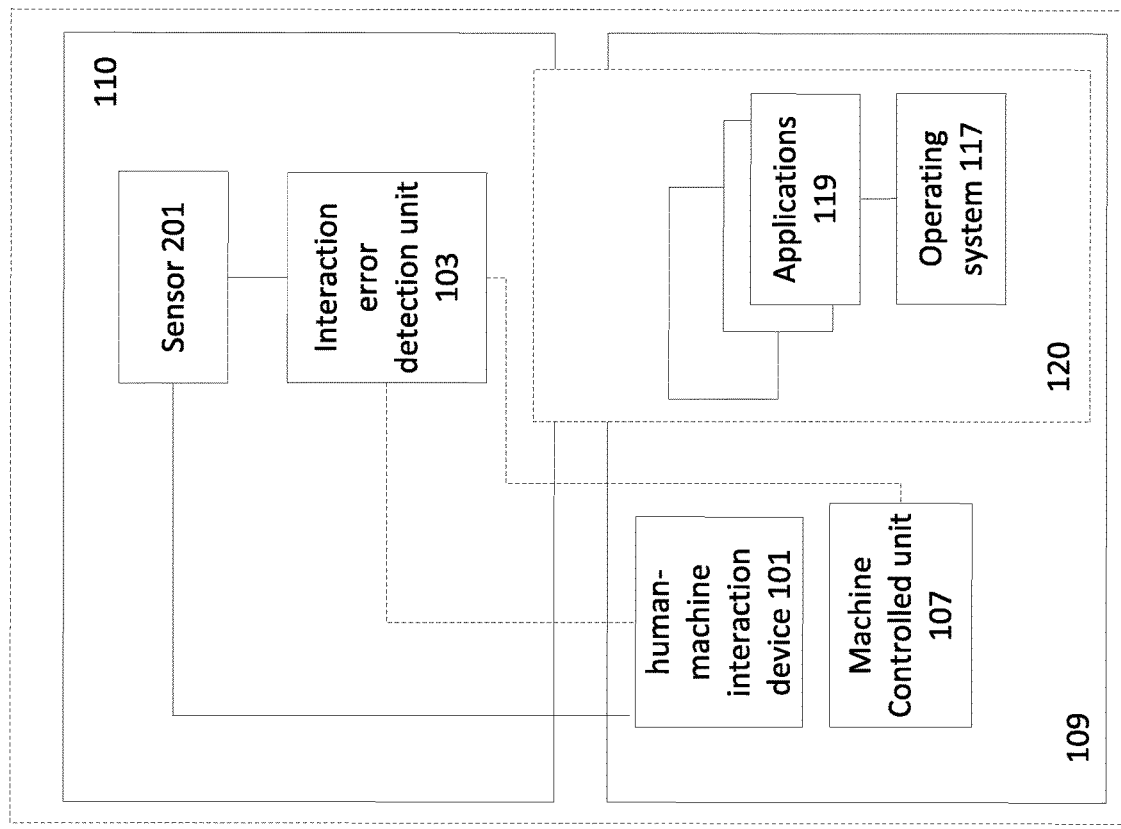
Fig. 2a
Fig. 2b

DETECTION OF HUMAN-MACHINE INTERACTION ERRORS

CROSS REFERENCE TO RELATED APPLICATION

This application is a continuation of U.S. patent application Ser. No. 15/321,619 filed Dec. 22, 2016, which claims priority to International Application No.: PCT/IL2015/050633, filed on Jun. 22, 2015, which claims priority to U.S. Provisional Patent Application No. 62/015,715 filed on Jun. 23, 2014, the contents of each of which are hereby incorporated in their entireties by reference.

TECHNICAL FIELD

The presently disclosed subject matter relates to the field of human-machine interaction.

BACKGROUND

Decision-making can be regarded as a cognitive process resulting in the conscious or unconscious selection from several possible alternatives. The final result of a decision-making process is a selected choice that may in some cases prompt an action.

Incorrect decisions (or incorrect actions resulting from such decisions) can result from internal cognitive errors made during the decision-making process. For example, decisions which are made under various sub-optimal conditions are prone to be incorrect. Sub-optimal decision-making conditions include for example, decision-making under pressure, decision-making absent-mindedly, decision-making in situations where uncertainty prevails, decision-making while being distracted or while performing multiple tasks simultaneously, and so forth.

Additionally, incorrect decisions (or incorrect actions resulting from such decisions) can also include decisions or actions which may have been initially correct but have become incorrect during or shortly after they were made. For example, this is so when a person making one decision makes a different (possibly converse) decision during or immediately after the initial decision was made. According to an additional example, this can result from a change which occurred in the objective reality, which rendered a previously made decision no longer relevant. Thus, a decision which may have been initially correct may become an incorrect decision due to a sudden change in the circumstances which led to the initial decision in the first place.

Incorrect decisions which are made in human-machine interaction scenarios are often followed by reactions which result in undesirable outcomes, which may have in some cases damaging and even devastating consequences. For example, when using a computerized device, such as a personal computer, a tablet or a smart phone, it is not uncommon that users perform erroneous actions such as: pressing the send button and sending an email, an SMS or another type of an electronic message to the wrong recipient or with inadequate content; deleting a file or folder (e.g. shift deleting or deleting where no backup is available); selecting "do not save" option when editing or closing a file; selecting "save" option when editing or closing a file; confirming the installation of undesirable and possibly malicious software; closing a browser window after rigorously searching for desired information or webpage; confirming a connection to an unreliable data resource; etc.

Incorrect decisions are also made by humans operating industrial instruments or machines. Such decisions may lead to incorrect actions which in some cases may result in injury or even death. For example, erroneous actions which are made by operators of various blades, saws, nail guns, heavy machinery or any other potentially hazardous machines. Incorrect decisions are also made while operating a vehicle (e.g. driving a land or marine vehicle or flying an aircraft), errors which in many cases result in severe consequences.

GENERAL DESCRIPTION

As explained above, incorrect decisions or resulting incorrect actions can include decisions and actions which may have been initially correct but have become incorrect during or shortly after they were made. Consider for example, a person or animal surprisingly jumping in front of a moving car. Once the driver sees the intruding person or animal intercepting the pathway of the car, a different decision (e.g. to hit the breaks or swerve the car) is made by the driver rendering the initial decision (to step on the gas pedal) to be an incorrect (or irrelevant) decision.

Additionally when operating a computerized device or when in contact with a computerized device, it is not uncommon that while a user is processing in his mind data presented by the computerized device (whether or not the user is interacting or preparing to interact with the computerized device) a change occurs to the presented data. For example, such a change may include an advertisement or a request to have software installed, which is suddenly presented on the computerized device display. The user is likely to respond to the new event e.g., by moving his/her eyes towards the newly presented content, a response which is often an instinctive reaction of the mind to the presented data. Often, immediately after the user reacts to the presented content (e.g. moves his pupils and/or eyes towards the content) he regrets the reaction and may also respond with a converse action (e.g. move his pupils and/or eyes away from newly presented content). Thus, such undesirable reactions of the user can be considered an incorrect action resulting from an incorrect decision.

Notably, this example demonstrates that an incorrect decision and a resulting action may occur also when the interaction between the user and the machine is not necessarily a physical interaction involving an action exerted by the user which has a direct effect on the machine (in the above example the interaction is the observation of the display device which does not necessary affect the computer device).

Similarly, incorrect decisions or resulting incorrect actions can include the reactions of a person to machine performance, while the person is not operating the machine but is only observing its operation (e.g. in order to verify that the machine is operating properly).

According to one example of the presently disclosed subject matter, differences can be detected between measured values (referred to herein as "command related data" as explained below) characterizing the reaction of the user to the errors made by the machine, and measured values characterizing the reaction of the user to the proper operation of the machine ("command related reference data"). Although the user is not operating the machine, the user has certain expectations as to how the machine is supposed to operate. The measured values characterizing the reactions of the user to the actual machine operation can be indicative as to whether the expectations are met or not.

The response of the user to an unexpected operation of the machine is considered an incorrect action as compared to the user's response when the machine operates as expected. If it is determined, based on the measured values, that the machine does not operate properly, this information can be used in various ways. For example the machine operations can be stopped automatically, amended, or improved in future machine operations.

Furthermore, according to the presently disclosed subject matter, incorrect decisions or resulting incorrect actions can include decisions or actions which did not yield the desired or expected result. For example, a person pressing an icon on a computer may expect a certain result from the icon press. The reaction of the user to the icon press may be different if the expected result indeed occurred as compared to the reaction of the user in case it did not.

Examples of unexpected or undesired results to an icon press include the following scenarios: the computer executes an unintended command, the computer responds too late, the computer does not respond at all, the computer partially responds or over responds (e.g., initiating too many events, playing an audio file too loud, presenting a too bright or too detailed interface, etc.). The undesirable or unexpected result renders the decision and/or action of the user incorrect.

Another example of this type of incorrect decision or resulting incorrect action can include the reaction of an operator to an incorrect machine reaction to an issued command (for example when operating a robotic arm and failing to control the arm in a desired manner). When a machine reacts to a certain command differently than what is expected by the operator (consciously or non-consciously), this discrepancy can prompt a human response which is considered erroneous as compared to the response when such discrepancy does not exist. As explained above, according to the presently disclosed subject matter, differences between measured values characterizing the user response can be indicative as to whether or not the machine operates in the desired or expected manner.

According to one aspect of the presently disclosed subject matter there is provided a method of detection of an interaction-error; the interaction-error is derived from an incorrect decision and is directed for interacting with a machine, the method comprising:

during human-machine interaction, obtaining command related data values characterizing any one of: an interacting-command; and an interacting-action; comparing the command related data values with command related reference data values; and identifying an interaction-error if a difference between the command related data values and the command related reference data values complies with a predefined criterion.

In addition to the above features, the method according to this aspect of the presently disclosed subject matter can optionally comprise one or more of features (i) to (xvi) below, in any desired combination or permutation.

(i). Wherein the interaction-error includes an erroneous interacting-command instructing a body part, interacting with human-machine interacting device, to perform one or more erroneous interacting-actions directed for controlling the machine for performing a desired machine operation.

(ii). Wherein the interaction-error includes an erroneous interacting-action performed by one or more body parts, interacting with human-machine interacting device for controlling the machine for performing a desired machine operation.

(iii). Wherein command related data includes one or more of the following types of data: EEG (electroencephalography) measured at the brain, EMG (electromyography) measured at a skeletal muscle of the at least one body part; kinematics measured at the at least one body part; kinematics measured at the human-machine interaction device; force, or derivative thereof, applied on the human-machine interaction device; time to lift of the at least one body part from human-machine interaction device; eye movement data; voice command data; facial muscles data; autonomic nervous system reaction data (including but not limited to the following parameters: cardiovascular, electrodermal, respiratory, which may be reflected but not limited to changes in heart rate, heart rate variability, blood pressure, blood pressure variability, blood flow, efferent postganglionic muscle sympathetic nerve activity (microneurography), skin electrical conductance or temperature, pupillary response (including differences between pupillary responses of the right and left eyes), eye blood vessels response and its derivatives, muscle tone etc.).

(iv). Wherein the method further comprises using one or more sensors connected to a human-machine interacting device; the human-machine interacting device is configured to enable interaction with the machine; the one or more sensors being configured to obtain command related data from the human-machine interacting device.

(v). Wherein the method further comprises using one or more sensors connected to one or more respective body parts used for interacting with a human-machine interacting device; the human-machine interacting device is configured to enable interaction with the machine; the one or more sensors being configured to obtain command related data from the one or more body parts.

(vi). Wherein the method further comprises generating the command related reference data.

(vii). Wherein command related reference data comprises one or more of: command related data statistics calculated based on command related data obtained from a population of users; command related data statistics calculated based on command related data obtained from a specific user; command related data explicitly indicated as being related to an interaction-error; and command related data patterns.

(viii). Wherein the method further comprises: determining a first command related data value at a first instant along an executed interacting-command or interacting action; based on the first command related data value, estimating an expected command related data value at a later instant along the executed interacting-command or interacting action; measuring command related data value at the later instant; if the difference between the expected command related data value and the measured command related data value complies with a predefined criterion, an interaction-error is determined.

(ix). Wherein the method further comprises measuring command related data with respect to one or more of: agonist muscle of the body part; and antagonist muscle of the body part.

(x). Wherein the interaction-command is a cognitive command intended to initiate a machine operation without physically interacting with a machine or a human-machine interacting-device connected to the machine.

(xi). Wherein command related data includes data indicative of cortical or sub-cortical activity parameters.

(xii). Wherein the interacting-action is a voice command and wherein the command related reference data comprises data relating to activity of speech related muscles.

(xiii). Wherein the interacting-action is a voice command and wherein the command related reference data comprises data relating to voice command related data patterns which are indicative of erroneous voice command; the method comprising: comparing between voice command related reference data patterns and (real-time) voice command related data patterns.

(xiv). Wherein the interaction-error includes an erroneous interacting-command instructing a bodily system, interacting with human-machine interacting device, to perform one or more erroneous interacting-actions responsive to an observed machine operation, wherein the interacting-actions do not have a direct effect on the operation of the controlled machine.

(xv). Wherein the interaction-error includes an erroneous interacting-action performed by a bodily system, interacting with human-machine interacting device, responsive to an observed machine operation, wherein the interacting-actions do not have a direct effect on the operation of the controlled machine.

(xvi). Wherein the interacting-action is initiated by the autonomic nervous system.

According to another aspect of the presently disclosed subject matter there is provided a system for detection of an interaction-error, the interaction-error being derived from an incorrect decision; the system being operatively connected to a controlled machine; the controlled machine being operatively connected to a human-machine interaction device is configured to enable user interaction with the controlled machine, the system comprising: an interaction-error detection unit operatively connected to at least one computer processor configured to:

obtain command related data values characterizing any one of: an interacting-command; and an interacting-action; compare the command related data values with command related reference data values; and identify an interaction-error if a difference between the command related data values and the command related reference data values complies with a predefined criterion.

According to another aspect of the presently disclosed subject matter there is provided a machine comprising a system for detection of an interaction-error; the interaction-error being derived from an incorrect decision; the system being operatively connected; the machine being operatively connected to a human-machine interaction device is configured to enable user interaction with the machine, the system comprising: an interaction-error detection unit operatively connected to at least one computer processor configured to:

obtain command related data values characterizing any one of: an interacting-command; and an interacting-action; compare the command related data values with command related reference data values; and identify an interaction-error if a difference between the command related data values and the command related reference data values complies with a predefined criterion.

According to another aspect of the presently disclosed subject matter there is provided a non-transitory program storage device readable by a computer, tangibly embodying a program of instructions executable by the computer to perform a method of detection of an interaction-error; the interaction-error is derived from an incorrect decision and is directed for interacting with a machine, the method comprising:

during human-machine interaction, obtaining command related data values characterizing any one of: an interacting-command, and an interacting-action; comparing the command related data values with command related reference data values; and identifying an interaction-error if a difference between the command related data values and the command related reference data values complies with a predefined criterion.

According to another aspect of the presently disclosed subject matter there is provided a computer program product implemented on a non-transitory computer useable medium having computer readable program code embodied therein for detection of an interaction-error derived from an incorrect decision and directed for interacting with a machine, the computer program product comprising:

computer readable program code for causing the computer to obtain, during human-machine interaction, command related data values characterizing any one of: an interacting-command; and an interacting-action;

computer readable program code for causing the computer to compare the command related data values with command related reference data values; and computer readable program code for causing the computer to identify an interaction-error if a difference between the command related data values and the command related reference data values complies with a predefined criterion.

In addition, the system, the machine, the program storage device and the computer program product can optionally comprise one or more of features (i) to (xvi) listed above, mutatis mutandis, in any desired combination or permutation.

According to another aspect of the presently disclosed subject matter there is provided a method, system, program storage device and computer program product for use for monitoring behavioral and operational patterns of a user and determining changes in such patterns and evaluating user performance.

According to another aspect of the presently disclosed subject matter there is provided a method, system, program storage device and computer program product for obtaining/calculating/determining command related reference data used in the detection of interaction-errors as disclosed herein.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 2A is a functional block diagram of a system, according to examples of the presently disclosed subject matter;

FIG. 2B is a functional block diagram of a system, according to examples of the presently disclosed subject matter;

Figure 1:
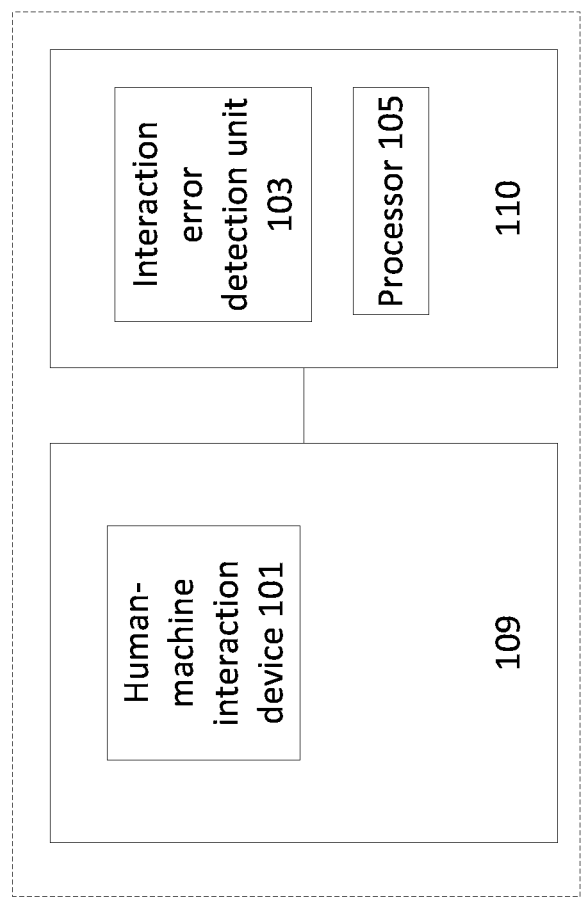
FIG. 1 is a general functional block diagram of a system, according to examples of the presently disclosed subject matter.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the invention. However, it will be understood by those skilled in the art that the present invention may be practiced without these specific details. In other instances, well-known features, structures, characteristics, stages, methods, procedures, modules, components and systems, have not been described in detail so as not to obscure the present invention.

System 110 and interaction-error detection unit 103, which are described below in detail, are computerized devices. The terms "computerized device", "computer", "controller", "processing unit", "computer processor" or any variation thereof should be expansively construed to cover any kind of electronic device with data processing capabilities, such as a hardware processor (e.g. digital signal processor (DSP), microcontroller, field programmable circuit (ASIC), etc.) or a device which comprises or is operatively connected to one or more hardware processors including by way of non-limiting example, a personal computer, server, laptop computer, computing system, a communication device and/or any combination thereof.

Unless specifically stated otherwise, as apparent from the following discussions, it is appreciated that throughout the specification discussions utilizing terms such as "comparing", "identifying", "determining", "measuring" or the like, include action and/or processes of a computer that manipulate and/or transform data into other data, said data represented as physical quantities, e.g. such as electronic quantities, and/or said data representing the physical objects.

The operations in accordance with the teachings herein may be performed by a computer specially constructed for the desired purposes or by a general purpose computer specially configured for the desired purpose by a computer program stored in a non-transitory computer readable storage medium. The presently disclosed subject matter further contemplates a machine-readable memory tangibly embodying a program of instructions executable by the machine for executing the disclosed method.

The term "non-transitory" made with reference to computer memory is used herein to exclude transitory, propagating signals, but to otherwise include any volatile or non-volatile computer memory technology suitable to the application including, but not limited to: hard disk, optical disk, CD-ROMs, magnetic-optical disk, magnetic tape, flash memory, magnetic card, optical card, any other type of media suitable for storing electronic instructions and capable of being coupled to a system bus, a combination of any of the above, etc.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) is included in at least one embodiment of the presently disclosed subject matter. Thus the appearance of the phrase "one case", "some cases", "other cases" or variants thereof does not necessarily refer to the same embodiment(s).

It is appreciated that, unless specifically stated otherwise, certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable sub-combination.

In various examples in accordance with the presently disclosed subject matter, fewer, more and/or different stages than those shown in FIGS. 4, 5, 6 and 7 may be executed. According to some examples of the presently disclosed subject matter one or more stages illustrated in FIGS. 4, 5, 6 and 7 may be executed in a different order and/or one or more groups of stages may be executed simultaneously, FIGS. 1, 2a, 2b and 3 illustrate a general schematic of the system architecture in accordance with examples of the presently disclosed subject matter. Functional elements in FIGS. 1, 2a, 2b and 3 can be made up of any combination of software and hardware and/or firmware that performs the functions as defined and explained herein. Functional elements in FIGS. 1, 2a, 2b and 3 may be centralized in one location or dispersed over more than one location.

Functional elements illustrated in FIGS. 1, 2a, 2b and 3 described below are operatively connected together in any way which is known in the art including, but not limited to, one or more of: serial connection, parallel connection, wired connection, and/or wireless connections.

It should be noted that the term "criterion" as used herein should be expansively construed to include any compound criterion, including, for example, several criteria and/or their logical combinations.

Bearing the above in mind, attention is drawn to FIG. 1 illustrating a general functional block diagram of a system, according to examples of the presently disclosed subject matter. In human-machine interaction scenarios, decisions made by a human often result in one or more cognitive commands intended to generate a specific machine operation. Commands generated in human-machine interaction scenarios (referred to herein as "interacting-commands") include commands to various parts of different systems of the human body (bodily systems such as: nervous system, cardiovascular system, muscular system, etc.) which occur in response to interactions of a human with a machine.

The human-machine interaction can be either an interaction which has a direct effect on the machine operation or an interaction which does not have a direct effect on the machine operation (e.g. human machine interaction involving only the observation of the operation of a machine).

Interaction-commands include motor-commands instructing a body part interacting with the machine to perform one or more actions (referred to herein as "interacting-actions") that may or may not be directed for controlling the machine for performing a desired machine operation. Interacting-actions include conscious interacting-actions and non conscious interacting-actions as well as discrete interacting-actions and continuous interacting-actions.

Interacting-commands are not limited to motor-commands and also include commands which do not result in a physical reaction of a body part i.e. of the muscular system. For example, brain-computer interface devices (abbreviated BCI and also known as "human-machine interface") are human-machine interface devices which provide a direct communication pathway between the brain of a user and an external device and enables a human to control the external device by cognitive commands intended to initiate machine operation without physically interacting with the external device.

As explained above, incorrect decisions are often followed by reactions which may result in undesirable outcomes. It is suggested that a person's mind is capable of identifying incorrect decisions, before the person is consciously aware of the error. In response to identification of an incorrect decision and/or a related erroneous command, the human mind compensates for it (e.g. inhibits/cancels and/or replaces/corrects the error) in attempt to reverse the decision and avoid the execution of the erroneous command or at least reduce its effect.

Detection of incorrect decision and/or actions, cancellation and/or correction attempts are reflected by a mental process characterized by a cascade of events; this begins with increased activity in regions associated with action/thought control (e.g. electrophysiological indices such as the error-related negativity, evoking from the medial frontal cortex or theta band oscillations in the right inferior frontal cortex), and/or the rise of competing events (e.g., a change in lateralized readiness potential). Cancellation and/or correction are further reflected by reduced activity in regions associated with the unwanted event and/or increased activity in regions associated with the new event. Reactions to an incorrect decision and/or actions and/or the compensation or correction process also involve bodily systems reactions such as reactions of the autonomic nervous system (e.g. detectible changes to pupil dilation).

As a result of such compensation, measurable parameters (referred to herein as "command related data"), which characterize an erroneous interacting-command and/or a resulting erroneous interacting-action are different than those of a correct-command and/or a resulting correct interacting-action.

According to the presently disclosed subject matter, one or more types of command related data can be measured before (e.g. during a response selection process), during and/or immediately after an interacting-command is performed. Based on the measured data it can be determined whether an interacting-command is an erroneous-command (e.g. an interacting-command driven by an incorrect decision) or a non-erroneous command (e.g. correct, driven by a correct decision).

The term "erroneous interacting-action" as used herein refers to an interacting-action initiated by an erroneous interacting command and the term "correct interacting-action" refers to an interacting-action initiated by a non-erroneous interacting-command. In the following discussion the term "interaction-error" is used as a general term to include any one of: incorrect decision, erroneous-interacting-command and erroneous interacting-action.

As described below in more detail, in response to detection of an interaction-error, various preventative actions can be carried out in order to abort, correct or otherwise react to any resulting machine operation.

Reverting to FIG. 1, interaction-error detection system 110 depicted in FIG. 1 comprises interaction-error detection unit 103. According to some examples, interaction-error detection unit 103 is operatively connected to human-machine interaction device 101.

Human-machine interaction device 101 is operatively connected to a controlled machine 109 and is configured to enable user interaction with the machine. Human-machine interaction device 101 can be configured as an integral part of the controlled machine 109 or alternatively it can be externally connected to the machine 109. Similarly, system 110 can be configured as an integral part of controlled machine 109 or alternatively it can be externally connected to the machine 109.

The term "controlled machine" as used herein should be broadly construed to include any type of machine or system powered by any type of power source (e.g. mechanical, chemical, electrical, thermal, etc.) including both computerized machines which are controlled by a computer system, a computer processor, a controller (including computer systems per se) as well as manually controlled machines. Optionally, an electronic command unit can be added to a manually controlled machine for enabling to electronically control the machine and interfacing with interaction-error detection system 110.

Human-machine interaction device 101 may enable direct interaction, where there is direct contact between a human body part and a human-machine interaction device 101 (e.g. by pressing a mouse button or pulling a lever) as well as indirect interaction where direct contact between a human body part and a human-machine interaction device 101 is not required (e.g. interacting with a gesture based touch-less interface, a voice command interface or BCI device).

Depending on the specific type of machine, human-machine interaction device 101 can include any suitable type of interaction device configured to input data and/or control a respective machine, including, but not limited to, any one of the following devices:

computer keyboard, computer mouse, touch-screen, touch-pad, mechanical or electronic lever, mechanical or electronic button, mechanical or electronic switch, mechanical or electronic knob, mechanical or electronic trigger, mechanical or electronic paddle, gesture based touch-less computer interface operated by any type of body part (e.g. based on a camera and a computer screen), eye movement computer user-interface, voice command computer user-interface, BCI, etc.

As mentioned above, according to the presently disclosed subject matter, human machine interaction also includes interactions which do not necessarily have a direct effect on the operation of the machine (e.g. when the interaction includes only the observation of the user on the machine performance). Thus, according to the presently disclosed subject matter, a human-machine interaction device can further include a display device (e.g. a computer device screen) which is used by the user for observing the output of the machine operations. Furthermore, according to some examples, controlled machine 109 itself is also the human-machine interaction device 101. For example, this is the case when an operator is observing the operation of a machine and the only interaction of the human with the machine is through the observation. The command related data pertaining to the reactions of the operator to the observed operation of the machine can be monitored and used for detecting interacting-errors.

Interaction-error detection unit 103 is configured to use command related data to determine whether a given interacting-command is an erroneous-command or not. Additionally, interaction-error detection unit 103 can be configured to use command related data to determine whether a given interacting-action, exerted with respect to a human-machine interacting device in response to an interacting-command, is an erroneous interacting-action or not. The functionality of interaction-error detection unit 103 depends, inter alia, on the type of the command related data which is analyzed.

According to the presently disclosed subject matter, command related data measured in relation to an interacting body part can be measured in both agonist muscle and antagonist muscle. In general, antagonist muscles exhibit an opposite effect to that of a respective agonist. Measuring command related data at antagonist muscles allows detection of erroneous interacting-actions even after the action of the agonist muscle is terminated, thus, potentially providing longer time for identifying erroneous-commands and/or erroneous-actions. Furthermore, by using command related data obtained from both agonist and antagonist muscles, a more accurate indication as to whether a command and/or action is erroneous or not, may be obtained.

Command related data includes for example any one of the following parameters and/or their derivatives or any combination thereof:

Electromyography (EMG) data which provides information related to electrical activity produced by skeletal muscles participating in an interacting-action. The electric activity measured at a skeletal muscle which is involved in an interacting-action is different when erroneous interacting-action is performed as compared to non-erroneous (e.g. correct) interacting-actions.

In general, EMG values, measured at an agonist muscle, decrease when the interacting-action is a result of an erroneous-command as compared to an interacting-action which results from a correct-command. EMG values, measured at an antagonist muscle, may also exhibit decreased values or, alternatively, under certain conditions, exhibit the opposite effect and thus show an increase in an interacting-action resulting from an erroneous-command.

Kinematics measured in relation to the body part participating in the action. Kinematics includes for example velocity of the body part when performing an interacting-action, acceleration of the body part when performing an interacting-action, deceleration when performing an interacting-action, etc. The kinematics measured when erroneous interacting-action is performed are different to those measured when a non-erroneous (e.g. correct) interacting-action is performed.

An interacting-action performed by an agonist muscle of a body part can be divided into three phases. An acceleration phase during the initial stages of the action, a constant velocity phase, and a deceleration phase during the final stage of the action. Command related data can be measured during any one of these phases, including for example acceleration measured during the first phase, constant velocity during the intermediate phase and deceleration of the agonist muscle during the final phase. Likewise, antagonist muscles of a body part performing an interacting-action exhibit similar phases occurring in opposite order. Thus, similar parameters can be measured with respect to an antagonist muscle.

For example, acceleration, measured at an agonist muscle, decreases faster when the interacting-action is a result of an erroneous-command as compared to an interacting-action which results from a non-erroneous command. Acceleration values, measured at an antagonist muscle, may show reduced activity in some cases and exhibit increased activity in other cases.

Kinematics measured in relation to the human-machine interacting device, responsive to an interacting body part. Kinematics includes for example velocity of the interacting device when responding to an interacting-action, acceleration of the interacting device when responding to an interacting-action, deceleration of the interacting device when responding to an interacting-action, etc. The kinematics measured when erroneous interacting-action is performed are different to those measured when an interacting-action resulting from a non-erroneous command is performed.

According to the presently disclosed subject matter the derivative of acceleration/deceleration in relation to time (also known as "jerk" or "jolt") can be used as an indication of an erroneous interacting-action. According to one example, the time period of an interacting-action can be divided into multiple bins, each representing a fraction of the time period. The acceleration/deceleration in each bin can be measured and represented by a respective value (e.g. the average acceleration/deceleration value or maximal acceleration/deceleration value). The jerk can be determined as the rate of change between acceleration/deceleration values in different bins.

Force (or any derivative thereof such as pressure) applied by the body part (on an interacting-device) when performing the action. In general, the force applied when erroneous interacting-action is performed is different than the force applied when a non-erroneous interacting-action is performed. The applied force can be measured on the interacting human body part which is applying the force or on the human-machine interacting device on which the force is being applied. Similar to the acceleration and jerk mentioned above, the rate of change in the applied force can be calculated and used as an indication of an erroneous interacting-action. Generally the applied force, measured at an agonist muscle, decreases when the interacting-action is a result of an erroneous-command as compared to an interacting-action which results from a non-erroneous (e.g. correct) command. Applied force measured at an antagonist muscle, shows the same effect in some cases, and exhibits the opposite effect in other cases.

Time to lift—a period of time before the body part is lifted from the human-machine interaction device on which the interacting-action is applied or period of time before the pressure applied on the human-machine interaction device is alleviated or period of time before the electric circle closed by the interacting action, opens again. For example, a time to lift period can be measured from the moment of initial contact of a body part with the human-machine interacting device until the body part is lifted from the human-machine interacting device. In general lifting time shortens when the interacting-action is a result of an erroneous-command as compared to an interacting-action which results from a non-erroneous command.

Furthermore, in some cases the interacting body part is not separated from the human-machine interacting device between one interacting-action to the next. This is so, for example, where a Swype keyboard is used which allows dragging a finger around a keyboard (or a touch screen) from letter to letter, without lifting the finger up and disconnecting the finger from the keyboard, and tapping a different key. In such cases lifting time can be measured from the initial contact with a certain key (or any other displayed object) until the time the finger is disconnected from the key and swiped sideways to a different key.

Command related data further includes additional parameters which can be measured directly in the brain and are similarly affected as a result of an erroneous-command, including for example:

Electroencephalography (EEG) is the recording of electrical activity along the scalp. The EEG data measured during an erroneous-command is different than the EEG data measured while a correct-command takes place. One EEG component data which has been shown to differ in these two different scenarios is error-related negativity (ERN). It has been shown that ERN values generally increase during brain activity related to an erroneous-command as compared to brain activity related to a correct-command.

In cases where the error involves a complex movement involving several limbs, the ERN value which is proportional to the motor representation of the erring limb can be used to specify which part of the movement is incorrect.

Another EEG activity which has been shown to differ in these two different scenarios (erroneous interacting and correct interacting) is motor neurons spike rate (MNSR). A decrease in the MNSR can be indicative of an attempt to prevent the error while an increase in the MNSR can be indicative of an attempt to correct the error. A combination of the ERN with MNSR reduction or other indices of motor response inhibition such as EEG correlates of response inhibition including N200 or theta band oscillations may yield a better indication of an error than each of these indices alone. A decrease in motor activity such as MNSR, EMG, or muscle activation following an attempt to prevent erroneous interacting-action is sometimes specific to the motor activation associated with the erring limb. The specificity of the error-related motor decrease may serve to indicate which part of the movement is incorrect.

Additional examples of parameters which may exhibit deferential values when measured during an erroneous-command as compared to a non-erroneous command include for example, diffusion magnetic resonance imaging and magnetoencephalography (MEG).

Different types of command related data allow detection of interaction-errors at different stages of the reaction. Cerebral activity detection methods (e.g. EEG and MEG) can be used for detecting an erroneous-command at an early stage before (e.g. during a response selection process occurring in the brain) or immediately after an interacting-command is generated. EMG data, which is measured at the skeletal muscles, at an early stage of the muscular response to a motor-command, allows early detection of an erroneous interacting-action resulting from an erroneous-command. Kinematics measured at the body part executing the reaction allows detection of an erroneous interacting-action at a later stage than EMG data. Command related data which is measured with respect to the human-machine interaction device (e.g. such as kinematics, "time to lift" and/or force exerted on the human-machine interaction device) allows detection of an erroneous interacting-action at later stages of a response to an interacting-command.

Command related data which is measured with respect to autonomic nervous system reactions to interaction-errors is usually measured at later stages of the motor command, which usually (unless the response is continuous) occur after the muscle activation related to the interaction-error has already been terminated. However, such autonomic nervous system reactions are usually faster than a deliberate compensatory action (e.g. corrective key press).

The specific autonomic nervous system response to an interaction-error usually precedes the development of an aware emotional response such as frustration. Current models of autonomic nervous system reaction describe a central nervous system coordination of autonomic activity (i.e., central-autonomic network). This results in a high degree of specificity in autonomic nervous system organization, allowing precise and fast adaptation to changes in both internal and external states. Parameters which may exhibit deferential values when measured close to an erroneous-command as compared to a non-erroneous command usually reflect a shift from parasympathetic control to sympathetic control over the nervous system. This can be reflected by, but is not limited to, larger skin conductance response, and greater heart-rate deceleration. Also, pupil size measurements show a more prominent dilatory effect following an error. Autonomic nervous system response to erroneous commands may also differ from autonomic nervous system response to a correct command or from autonomic resting state in the rate of change in autonomic nervous system response, wherein the rate of change is larger in response to interaction error.

System 110 can further comprise one or more computer processors 105. According to one example, interaction-error detection unit 103 can comprise computer memory being operatively coupled to computer processor 105 configured to execute instructions generated by interaction-error detection unit 103 and control its operation. According to another example, interaction-error detection unit 103 and computer processor 105 can be configured as a single processing device (e.g. configured as an application specific integrated circuit (ASIC)). Computer processor 105 can be a processor dedicated for executing the operations of interaction-error detection unit 103 or it can be a general computer processor e.g. operatively connected also to controlled machine 109 configured to execute its respective operations.

As mentioned above, interaction-error detection unit 103 can be configured, responsive to detection of an interaction-error, to execute one or more actions in order to confirm or abort any machine operation (including any operation of a computerized device or system) resulting from an erroneous interacting-action, or otherwise acknowledge or alert that an interaction-error has occurred. Alternatively, if the interaction-error is a result of a machine operation, unit 103 can be configured, responsive to detection of an interaction-error, to execute one or more actions in order to confirm or abort any machine operation (including any operation of a computerized device or system) resulting from the erroneous interacting-action, or otherwise acknowledge or alert that an interaction-error has occurred. Actions can include for example any one or more of the following:

Activating an alert for alerting the user or a third party, delaying the requested machine operation, requesting confirmation from the user to proceed with the machine operation (e.g. prompting a dialog box indicating the detected error and requesting confirmation from the user), canceling the execution of the machine operation, automatically executing an alternative command (e.g. where only two machine operations are available-executing the alternative option), recording the error, etc.

Proceeding to FIG. 2a and FIG. 2b, each show a functional block diagram of a system, according to examples of the presently disclosed subject matter. FIGS. 2a and 2b illustrates examples of interaction-error detection system 110 operatively connected to (or otherwise integrated as part of) controlled system 109.

According to an example of the presently disclosed subject matter, command related data can be obtained with the help of one or more sensors 201 of one or more types. Depending on the type of command related data which is used, one or more suitable sensors, configured for retrieving the sought after command related data, are used. Sensor 201 is operatively connected to unit 103 and is configured to feed unit 103 with the acquired sensing data.

In some examples sensor 201 can be connected to human-machine interaction device 101 (as illustrated in FIG. 2a) in order to retrieve command related data which is generated by the direct interaction of the user with human-machine interaction device 101. This is so, for example, when command related data is any one of the following parameters: force (or any derivative thereof) applied on the human-machine interaction device, velocity of the human-machine interaction device, acceleration or deceleration of the human-machine interaction device, time to lift, etc.

For example, when a user is using a computer mouse and/or a keyboard (i.e. the computer mouse and/or keyboard being the human-machine interaction device) and the measured command related data is related to the force applied by the finger when pressing the mouse button and/or a key in the keyboard, sensor 201 can be a force sensor (e.g. a force-sensing resistor or a piezoelectric sensor) installed underneath the mouse button or underneath the keyboard keys.

If the measured command related data which is used for identifying interaction-errors is related to the acceleration and/or deceleration of the mouse button (or keyboard key) when it is being pressed, sensor 201 can be an accelerometer (e.g. piezoelectric accelerometer or semiconductor accelerometer material) configured for measuring the acceleration and/or deceleration of the mouse button (or different keys in the keyboard). Similar to the force sensor, the accelerometer can be installed underneath the mouse button (or the keyboard keys).

In other examples sensor 201 may not be connected to human-machine interaction device 101 (as illustrated in FIG. 2b). This is so, for example, when command related data is measured directly from the body part of the user interacting with human-machine interaction device 101. For instance when command related data is related to the acceleration and/or deceleration of the body part which is interacting with human-machine interaction device 101, sensor 201 is an accelerometer attached to the body part (e.g. an accelerometer attached to hand or foot controlling human-machine interaction device 101).

In an additional example, sensor 201 may also not be directly connected to human-machine interaction device 101 where measured command related data is related to EMG data measured by an electromyograph attached to a body part of the user. An electromyograph is an instrument that detects the electrical potential generated by muscle cells when these cells are electrically or neurologically activated. The electrodes (sensors) are commonly connected to a monitored body part in one of two ways. The first is with EMG sensors, which are connected to the surface of the skin, and the second is with intramuscular EMG, where a needle electrode or a needle containing two fine-wire electrodes is inserted through the skin into the muscle tissue. The sensed electric activity is transmitted to unit 103 where it is used for determining whether the action is erroneous or not. EMG sensors can be connected to either or both agonist and antagonist muscle.

Sensor 201 may not be directly connected to human-machine interaction device 101 where measured command related data is based on a cerebral activity detection method such as EEG.

In another example, sensor 201 may also not be directly connected to human-machine interaction device 101 where measured command related data is measured directly from the body part of the user and the body part does not necessarily directly affect the operation of the machine. For example, where reactions of a bodily system are monitored while the user is observing the operation of the machine and the monitored values are used for detecting interacting-errors. According to a specific example, this is so where an operator is observing output displayed on a computer display device. The sensor device can be a camera monitoring eye movement and/or changes in pupil diameter or eye blood vessels, the changes providing the relevant command related data. Likewise, the sensor device can be a watch or bracelet strapped around the wrist of the user and used for measuring skin electrical conductance.

Communicating between sensor device 201 and unit 103 can be facilitated using a wired communication device or wireless communication device. Sensor device 201 can take various forms designed for obtaining the desired command related data from an interacting body part. For example, sensor device 201 can be designed as a strap worn around an arm or a foot of a user. The strap can contain an appropriate sensor (e.g. electromyograph electrode or accelerometer) which can be positioned conveniently for monitoring the interacting body part. The strap can further contain a wireless communication device configured to transmit the obtained command related data to unit 103. In a similar manner sensor device 201 can be designed as a glove worn on a hand or sock worn on a foot, equipped with wireless communication technology for communicating with unit 103 and transmitting the acquired command related data.

As mentioned above with reference to FIG. 1, in some examples interaction-error detection unit 103 is connected to human-machine interaction device. However, this is not always necessary. For example, in case command related data is obtained by a sensor connected to a user's interacting body part, interaction-error detection unit 103 can be connected to machine controlled unit 107 for controlling machine operation and may not be connected to human-machine interaction device 101.

A special sensor unit may not always be necessary for the operation of interaction-error detection unit 103. This is so, for example, when command related data is based on "time to lift". While in some cases, a sensor is required in order to determine whether there is contact between human-machine interaction device 101 and a body part of the user, in other cases this is not necessary. For example, the time length of a key press (i.e. time to lift) on a keyboard can be measured using Application Programming Interface (API) functions provided by the operating system of a computer. The API functions are executed using a computer processor configured for executing operating system instructions.

Optionally, a combination of different types of sensors (e.g. including both sensors connected to human-machine interaction device 101 and others not connected to human-machine interaction device 101) each measuring a different type of command related data, can be used together.

Controlled machine 109 and/or system 110 can further comprise or be otherwise operatively connected to computer data storage 120 (possibly including both transitory and non-transitory computer memory) operatively connected to one or more computer processors, configured to execute computer programs stored thereon. According to some examples of the presently disclosed subject matter, computer data repository 120 can store, inert cilia, computer programs configured with instructions for controlling human-machine interaction device 101 and/or computer programs configured for controlling interaction-error detection unit 103.

Data repository 120 can further comprise various applications including for example, one or more operating systems 119 (e.g. Microsoft Windows, Linux, Unix, Mac OS), as well as various other applications 117 such as:

one or more file systems; one or more Internet browsers (e.g. Internet Explorer, Mozzila Firefox, Google Chrome, etc.); one or more personal information managers applications (e.g. Microsoft Outlook, Google Calendar, etc.); one or word processing applications (e.g. Microsoft Word Processor, OpenOffice, etc.); one or more media players; and so forth.

According to some examples of the presently disclosed subject matter, interaction-error detection unit 103 can be operatively connected to one or more operating systems and/or one or more other applications running on controlled machine 109 and be configured to monitor and control the operation of the operating system and/or applications. Interaction-error detection unit 103 can be configured, responsive to detection of an interaction-error, to delay or abort the execution of a requested machine operation and/or generate a warning indicating that an erroneous interacting-action has being detected (e.g. by displaying a dialog box on a display device connected to system 110).

According to other examples of the presently disclosed subject matter, interaction-error detection unit 103 can be directly connected to a machine controlled unit 107 (e.g. a circuitry and/or a controller) in controlled machine 109 for allowing interaction-error detection unit 103 to control the execution of commands generated by human-machine interaction device 101.

According to further examples of the presently disclosed subject matter, where controlled machine 109 is a manually operated machine, an auxiliary computerized device can be installed in controlled machine 109 to enable to electronically control the execution of operations initiated by human-machine interaction device 101. For example, when using a nail gun, an electronic unit mounted on the gun can be configured to electronically control the operation of the nail gun. Responsive to an indication of a detected interaction-error received from interaction-error detection unit 103, the electronic unit can be configured to temporarily lock a safety catch.

Figure 3:
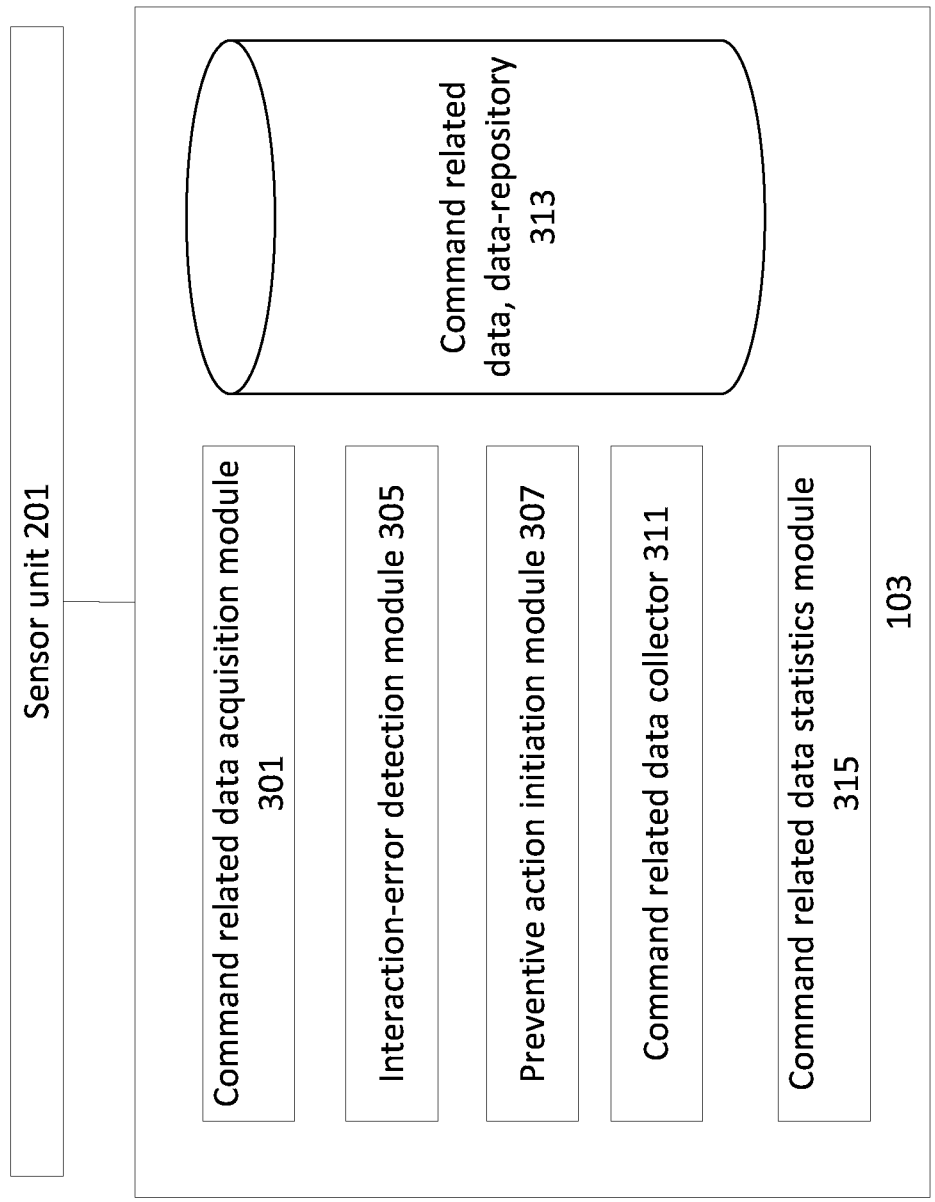
FIG. 3 is a functional block diagram of an interaction-error detection unit, according to examples of the presently disclosed subject matter.

FIG. 3 is a functional block diagram illustrating an example of interaction-error detection unit 103, in accordance with an example of the presently disclosed subject matter. According to the illustrated example, interaction-error detection unit 103 can comprise: command related data acquisition module 301 interaction-error determination module 305 and preventive action initiating module 307. Interaction-error detection unit 103 can further comprise or be otherwise operatively accessible to a computer data-repository 313 configured for storing command related data.

Command related data acquisition module 301 is configured to obtain command related data recorded during interaction of a user with a monitored human-machine interacting device. The data can be obtained from one or more sources. As explained above, command related data can be obtained from one or more sensors of various types which are connected to interaction-error detection unit 103 and/or from additional sources such as an operating system using operating system Application Programming Interface (API) functions.

Command related data acquisition module 301 can be further configured to process the raw data received from various sensors in order to extract desired data and/or to transform the data to a desired format (performing operations such as noise filtering, artifact rejection, etc.).

Interaction-error detection module 305 is configured to compare data obtained by command related data acquisition module 301 with command related reference data values.

To this end, data-repository 313 can comprise for example, threshold values for determining whether a given measured command related data value is indicative of an interaction-error. Interaction-error detection module 305 can be configured to compare the measured command related data values with the stored thresholds and determine if the comparison complies with one or more predefined criteria. Based on the results of this comparison, it is determined whether the measured command related data is indicative of an erroneous interacting-action.

For example, assuming "time-to-lift" parameter is used, data-repository 313 can store information with respect to a predefined time range characterizing a correct interacting-action (e.g. mouse button press). If the difference between the measured time to lift and the time-to-lift threshold is greater than a predefined value, an erroneous interacting-action is identified.

Preventative action initiating module 307 is configured to initiate one or more actions in response to detection of an erroneous-command. Optionally, the initiated action may be specifically adapted to each specific user. Where human-machine interaction device 101 is configured to execute an instruction responsive to an interaction-error, preventative actions can include instructions directed to human-machine interaction device 101 and/or to a controller and/or to a computer program controlling human-machine interaction device 101 for delaying or aborting the execution of the erroneous-command. If machine operation has already been executed by the time an interaction-error is detected, preventative actions can include instructions directed to human-machine interaction device 101 and/or to a controller and/or to a computer program controlling human-machine interaction device 101 for undoing, or replacing the outcome of the erroneous-command.

Where a device other than human-machine interaction device 101 itself is configured to execute a machine operation responsive to the interaction-error, preventative actions can include instructions directed to machine controlled unit 107 (e.g. a controller and/or to a computer program) configured to control the execution of the machine operation, for delaying or aborting the execution of the machine operation. If machine operation has already been executed by the time an interaction-error is detected, preventative actions can include for example instructions directed for undoing, or replacing the outcome of the error.

For example, assuming human-machine interaction device 101 is a keyboard or a mouse connected to a computer device, preventative action initiating module 307 can be operatively connected to an operating system and/or to an application which is being monitored for interaction-errors. More specifically, assuming for example that Outlook program is being monitored by system 110 for interaction-errors, preventative action initiating module 307 can be operatively connected to an operating system or directly to Outlook. In response to an identified interaction-error, preventative action initiating module 307 can be configured to delay the execution of the machine operation (e.g. command to send a message or command to delete a message) and prompt a dialog box requesting the user for confirmation before the machine operation is executed. If a message has already been sent, preventative action initiating module 307 can be configured for example to abort or delete the sent message.

Optionally, interaction-error detection unit 103 can further comprise command related data collector 311 configured to obtain command related data and store the obtained data in data-repository 313. Examples of methods of determining command related reference data for detection of interaction-errors are described below with reference to FIGS. 5 to 7.

Figure 4:
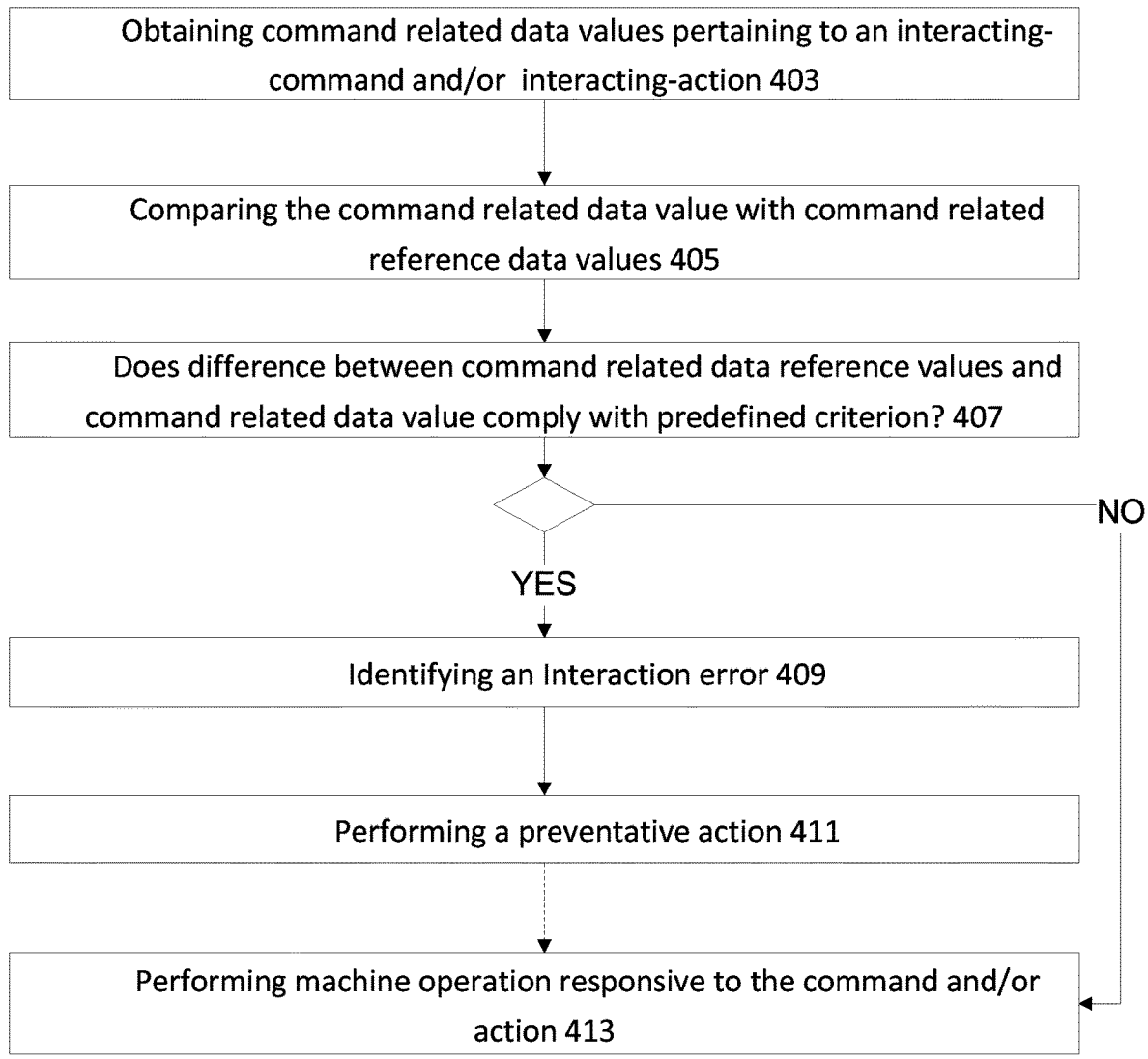
FIG. 4 is a flowchart showing operations performed, according to examples of the presently disclosed subject matter.

FIG. 4 is a flowchart of operations performed, in accordance with an example of the presently disclosed subject matter. Operations described with reference to FIG. 4 can be executed for example by system 110 with the help of interaction-error detection unit 103.

While a user is interacting with a human-machine interaction device, command related data is being collected. At block 403 command related data values are obtained from a monitored human-machine interaction device and/or monitored body part. As explained above, collection of command related data can be accomplished with the help of one or more sensors.

The command related data values obtained in real-time during interaction of a user with a human-machine interaction device is compared with command related reference data (block 405). Command related reference data can be presented as command related threshold values. As mentioned above, command related reference data values can be stored in a designated data-repository.

Based on the comparison between the measured command related data values and the command related reference data, it is determined whether the issued interacting-command and/or interacting-action represent an interaction-error (block 407).

If the difference between the measured command-related data values and the command related reference data values does not comply with some predefined criterion, the interacting-action is executed without interference (413). Otherwise, if the difference between the measured commands related data values and the command related reference data values complies with the predefined criterion, the interacting-command and/or interacting-action is determined as an interaction-error (block 409). As explained above, responsive to detection of an interaction-error, preventative actions can be executed (block 411).

In order to allow detection of interaction-errors and generate an appropriate response, the process of determination of an interaction-error is performed before, during and/or immediately after the interacting-command (and/or the resulting interacting-action) is performed to allow sufficient time for stopping or aborting a respective machine operation, if desired.

Optionally, the response time of the human-machine interaction device to a direct interacting-command or a resulting interacting-action can be made longer to allow sufficient time for determination of whether an interacting-command and/or interacting-action is erroneous before the respective machine operation is executed. For example, assuming human-machine interaction device 101 is a computer mouse connected to a computer device (being controlled machine 109), the response time of the computer device to the mouse input can be set to be 150 milliseconds long in order to ensure sufficient time for detection of an erroneous interacting-command and/or action. The response time is maintained fast enough to avoid significant slowdown and degradation of the user experience.

Similarly, the force (or pressure) and/or duration of force (or pressure) required to initiate a response from a human-machine interaction device can be increased in order to enable the collection of sufficient data for determination of whether an interacting-command and/or interacting-action is erroneous. Increasing the required force or prolonging its duration would compel a user to exert additional force or increase duration of force exertion when interacting with a human-machine interaction device and thereby provide more data to interaction-error detection unit 103.

Furthermore, any change made to the response time (or the required force) of a human-machine interaction device can optionally be adapted to a specific user. For example, normal user-specific command related data values can be calculated based on command related data collected during the interaction of a user with a given human-machine interaction device over time. Once the normal user-specific command related data is available, it can be used for determining user specific performance characteristics such as an average user-interaction velocity e.g. the average length of the time period a user maintains his hand or finger in contact with a human-machine interacting device during an interacting-action. Adaptation of the response time of a human-machine interaction device can be based on the calculated user-interaction velocity. A shorter prolongation of the response time is required where the user exhibits quicker responses, as compared to users who exhibit slower responses.

Identification of interaction-errors based on command related data can be used while various body parts are interacting with a human-machine interaction device. For example, in addition to commands issued by hands, fingers and feet, the same principles described herein can be used for determining interaction-errors issued by eye or head movement.

Today various systems which use eye (or pupil) movement human-computer interaction are available and other systems are being developed. One example is Samsung's Galaxy IV Smartphone which is equipped with an eye scroll feature allowing a user to scroll through a web page using only eye movement.

Human-machine interaction device 101 can be configured as an eye movement computer interface, including for example a camera operatively connected to appropriate eye movement analysis software.

Movement of the eyes is enabled and controlled by six muscles connecting the eye balls to the eye orbit. Electric activity (EMG) derived by eye movement can be detected using for example, two pairs of contact electrodes placed on the skin around the eye which allows identifying two separate movement components—horizontal and vertical.

Electric activity generated by eye (and/or head) movement as well as eye and/or head) movement kinematics measured for example through a camera recording head and eye movement and calculating kinematic parameters (including for example, velocity, acceleration, deceleration of eye movement, etc.) can be monitored and used for identification of interaction-errors.

For example, when eye movement tracking is used for human-computer interaction, saccade eye movements (which are quick, simultaneous movements of both eyes in the same direction) which follow an erroneous eye movement interacting command, are characterized by different command related data than those which follow a correct eye movement interacting command.

In general, agonist muscle eye movement of an erroneous interacting-action is weaker, slower, and is terminated quicker as compared to similar eye movement of a non-erroneous interacting-action. An antagonist muscle eye movement of an erroneous interacting-action is generally stronger and faster, than a similar eye movement of a non-erroneous interacting-action. Accordingly, command related data characterizing saccade eye movement can be used for identifying erroneous interacting-actions (in this case eye interacting movement).

Other muscles located around the eye which are in charge on the movement of various facial muscles (e.g. orbicularis oculi which closes the eye lids or corrugator supercilii which is related to the eyebrow movement) can also be monitored in a similar fashion.

In a similar manner, when eye tracking is used for human-machine (e.g. computer) interaction, changes in pupil diameter or eye blood vessels which follow an interacting-error are characterized by different command related data than those which follow a correct interacting command and/or action or those occurring at resting state. For example, such command related data includes the rate of change in autonomic nervous system response where, the rate of change (e.g. rate of change of pupil dilation, rate of changes in electric skin conductance, rate of change in eye-blood vessels diameter and/or eye-blood vessels color and/or eye-blood vessels blood flow, etc.) is larger in response to an erroneous command as compared to a correct command.

Another type of human-computer interaction method is by voice commands. Today many computer systems can be controlled by human voice command. Speech related muscles which are located in the larynx (e.g. phonatory muscles) enable the production of voice. Command related data (such as EMG data) with respect to these muscles can be measured and used for determining whether a given voice interacting command is erroneous or not.

Thus, according to the presently disclosed subject matter, when voice commands are used for interacting with a computerized device, voice command related data such as EMG data collected from the voice generating muscles, or voice patterns as explained herein below, can be used for determining whether a given voice interacting-command is an erroneous interacting-command or not. According to this example, human-machine interaction device 101 can be configured as a voice-based computer interface including for example a speaker operatively connected to an appropriate voice analysis processing unit.

Figure 5:
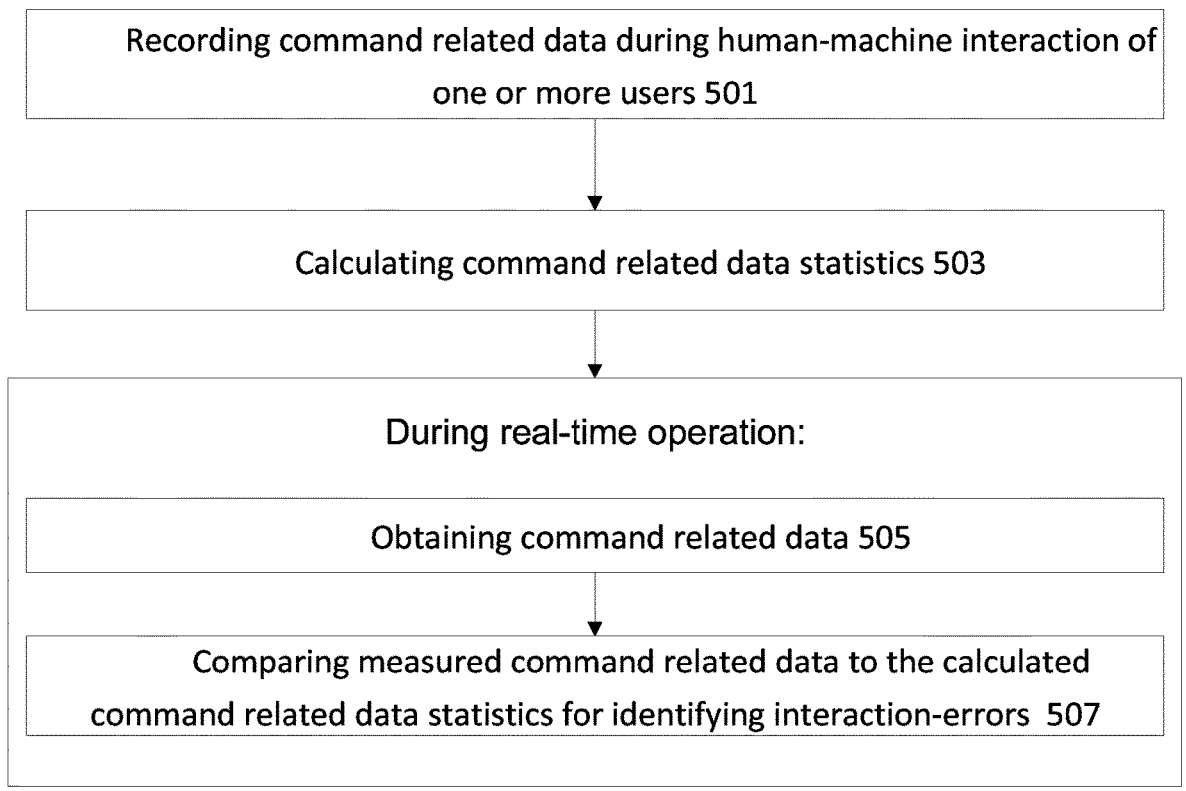
FIG. 5 is a flowchart showing operations performed for obtaining command related reference data, according to examples of the presently disclosed subject matter.

As mentioned above, various methods can be implemented for determining command related reference data values which enable to identify interaction-errors. FIG. 5 is a flowchart showing operations performed for obtaining command related reference data, according to examples of the presently disclosed subject matter. Operations described with reference to FIG. 5 can be executed by unit 103 (e.g. with the help of command related data collector 311 and command related data statistics module 315).

According to one example, human-machine interaction of one or more users with a given type of human-machine interaction-device is monitored and command related data parameters are recorded (block 501). Command related data statistics (e.g. average and standard deviation) of the recorded command related data can be calculated (block 503). The calculated command related data statistics can serve as command related reference data used for identifying interaction-errors. Calculated command related data statistics can comprise both reference data indicative of interaction-errors as well as reference data indicative of correct interacting-command and/or correct interacting-action. The calculated command related data statistics can serve as command related reference data used for identifying inter-action-errors.

Command related data can be recorded for a certain period of time or until a certain desired amount of data is recoded before it is used for calculating statistics. Command related data can be continuously recorded during human-machine interaction and used for enhancing the command related data statistics.

Command related data can be recorded according to various recording policies. For example, during the execution of specified tasks or applications, during a training period, when initializing the system, every few days, in the course of the last couple of days, couple of hours, and so on.

Command related data statistics can be calculated for various specific setups such as: a specific user, a specific group of users, specific types of human-machines interacting-devices, specific types of machines, specific types of applications and so forth.

Command related data can be recorded and stored during the interaction of a single user with a given human-machine interaction-device. This would allow calculating user-specific command related data statistics providing a personalized (user-specific) characterization of the user's performance. Additionally or alternatively, command related data can be recorded during the interaction of many different users all interacting with the same type of human-machine interaction device and/or the same machine and/or the same computer program, thus enabling to obtain normal command related reference data representing the distribution of command related data values in a monitored population of users. Normal command related reference data can be used for calculating normal command related data statistics, including for example the average and standard deviation of the command related data values collected from the population of users.

Both user-specific and population-specific command related reference data can be calculated by interaction-error detection unit 103 (e.g. with the help of command related data statistics module 315). In addition, interaction-error detection unit 103 or machine 109 connected thereto can be configured to send recorded command related data to a central computer server where command related reference data of all users is consolidated and stored and the command related data statistics can be calculated.

The obtained command related data statistics can be provided (e.g. sent from the computer server where they were calculated) to interaction-error detection unit 103. During real-time interaction of a user with a monitored machine 109 real-time command related data is obtained (block 505) and the calculated statistics can be used for identifying erroneous-command and/or erroneous interacting-actions (block 507). For example, command related data values measured during real-time interaction can be determined as indicative of an interaction-error based on pre-defined deviation from the calculated command related data statistics.

Command related reference data can be enhanced by additional data, including for example, command related data collected while an actual interaction-error is performed and corrected. A correction of an interacting-action which is made by the user provides an explicit indication that the interaction-error was erroneous. The command related data which is recorded during such a corroborated error can be used for obtaining additional information indicative of specific command related data values which characterize an erroneous interacting-action. Likewise, command related data recorded during a correct interacting-action can be used for obtaining additional information indicative of command related data values which characterize a correct interacting-action.

Corroboration of command related reference data can be obtained for example by prompting a user after an interacting-action is performed, asking the user whether the performed action was erroneous or not and/or by monitoring spontaneous user correction of interacting-actions and/or manual or voice gestures indicating an error.

Figure 6:
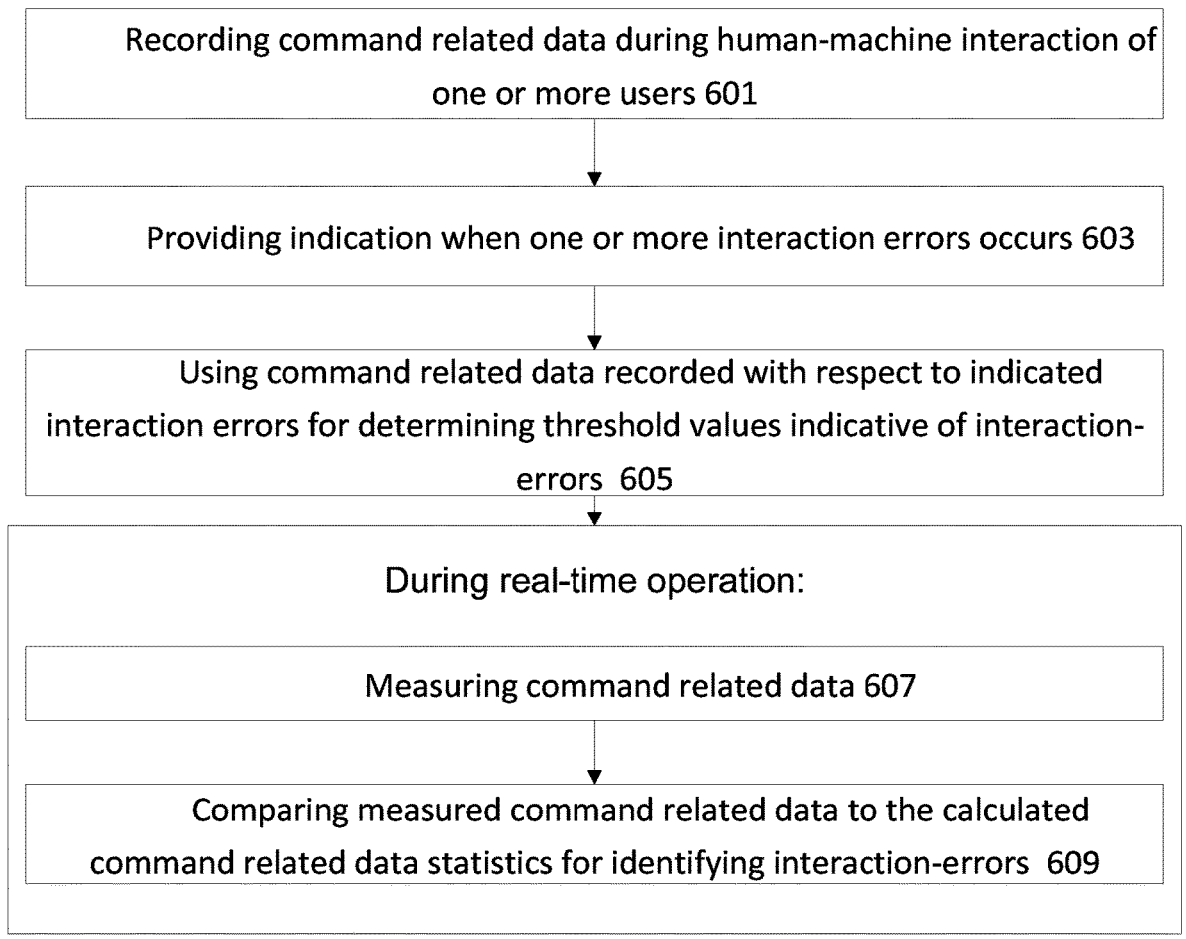
FIG. 6 is a flowchart showing operations performed for obtaining command related reference data, according to examples of the presently disclosed subject matter.

FIG. 6 is a flowchart showing operations performed for obtaining command related reference data, according to examples of the presently disclosed subject matter. Operations described with reference to FIG. 6 can be executed by unit 103 (e.g. with the help of command error data collector 311).

Similar to the previous example, the interaction with a given human-machine interaction-device is monitored and command related data parameters are recorded (block 601). During human-interaction with the machine, indication is provided when an interaction-error occurs (block 603). For example, during a training session the user can be instructed to actively indicate whenever an interaction-error is made. Alternatively, correction of an issued interacting-action can serve as an indication that the initial interacting-action was erroneous. The specific command related data characterizing a corrected interacting-action can be recorded and stored in data-repository 313 and used as reference for identifying interaction-errors in real-time operation of system 110. Command related reference data recorded in relation to interaction-errors can be used for determining threshold values indicative of interaction-errors (block 605).

During real-time interaction of a user with a monitored machine 109 command related data is determined (block 607) and compared to the threshold values for identifying interaction-errors (block 609).

Similar to the previous example, the interaction with a given human-machine interaction device is monitored and command related data parameters are recorded (block 601). During human-interaction with the machine, indication is provided when an erroneous-command and/or erroneous action occurs (block 603). For example, during a training session involving specific stimulus-response rules (e.g., stimulus A should be followed by user-response B, stimulus C should be followed by user-response D and so forth), a stimulus driven response that failed to follow the required response rule is indicated as an error. Alternatively or additionally, during a training session with or without stimulus-response rules, the user can be instructed to actively indicate whenever an interaction-error is made. Further, alternatively or additionally, during a training session involving specific stimulus-response rules, correction (replacement of a response that failed to follow the stimulus-response rule by an appropriate response or deletion of the response) of an issued interacting-action can serve as an indication that the initial interacting-action was erroneous. According to another example, in the absence of a stimulus-response rule, a correction by means of fast switch between responses (e.g., while using a Smartphone, pressing a function key and then pressing another key before or immediately after the function signified by the first pressed key is fully activated) or deletion of a response, may be made. Similar to the specific command related data indicating an interaction-error, the specific command related data characterizing a corrected interacting-action can be recorded and stored in data-repository 313 and used as reference for identifying interaction-errors in real-time operation of system 110.

Figure 7:
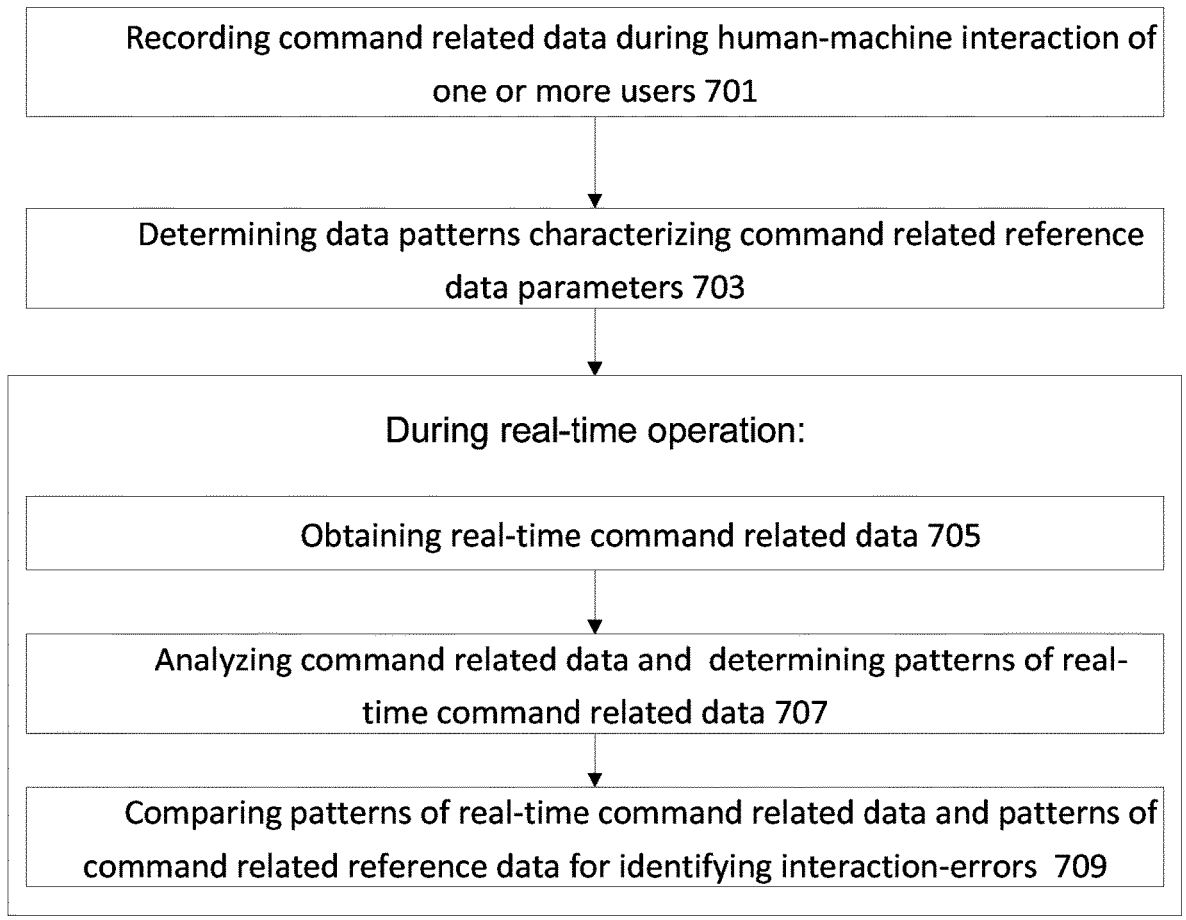
FIG. 7 is a flowchart showing operations performed for obtaining command related reference data, according to examples of the presently disclosed subject matter.

FIG. 7 is a flowchart showing operations performed for obtaining command related reference data, according to examples of the presently disclosed subject matter. Operations described with reference to FIG. 7 can be executed by unit 103 (e.g. with the help of command error data collector 311).

As before, the interaction with a given human-machine interaction-device is monitored and command related data parameters are recorded (block 701). Command related data values measured during the initial stages of an erroneous interaction-command and/or erroneous interaction-action may be close to the values measured during a correct erroneous interaction-command and/or a correct interaction-action. Thus, using command related data measured at the initial stages of the interaction may not be sufficient for identifying an interaction-error. However, as the interaction-command or and/or interaction-action progresses, the differences between command related data characterizing an interaction-error, and command related data characterizing a non-erroneous (e.g. correct) interaction, become more distinct.

Thus, according to the presently disclosed subject matter, the recorded command related data can be analyzed to determine patterns (referred to herein as "patterns" or "command related data patterns") characterizing the command related data (block 703). Command related data patterns represent variations in command related data values along the progression of a respective interaction-command and/or an interacting-action. Command related data patterns of command related data of non-erroneous (e.g. correct) inter-action-command and/or a non-erroneous (e.g. correct) inter-acting-action are different to those of incorrect interaction-command and/or an incorrect interacting-action. Thus, patterns can serve as command related reference data.

For example, if command related data relates to acceleration measured at an interacting-human body part, a respective pattern indicates the acceleration values along the progression of the interacting-command and/or interacting-action. The acceleration of interaction-error at the initial stages of the interaction may be similar to those of a correct interaction, however, as the interaction progress difference in acceleration between an interaction-error and a correct interaction become more distinct.

According to a different example, if command related data pertains to an autonomic nervous system reaction measured at the pupil, a respective pattern indicates the pupil dilation values along the progression of the interacting-command and/or interacting-action. The pupil dilation accompanying interaction-error at the initial stages of the interaction may be similar to those of a correct interaction, however, as the interaction progresses difference in pupil dilation, between a interaction-error and a correct interaction, become more distinct.

Furthermore, according to the presently disclosed subject matter, command related data may further include voice patterns of voice commands. As explained above, error compensation, in response to an incorrect decision, may also affect voice commands. Differences between voice patterns of an erroneous voice interacting-command and correct voice interacting-commands may be based on variations in the intensity, pitch, tone of voice and/or distance between spoken syllables within a word/spoken gesture or between words/spoken gestures (including complete interruption). Alternatively or additionally, a person's attempt to reverse an incorrect voice command can be inferred from spoken gestures generated very close to and/or immediately after the incorrect voice command.

For example, an erroneous voice interacting-command driven by an incorrect decision, may be characterized by a decreased gap between certain spoken syllables and/or words and/or vocal gestures within the command as compared to a similar gap in a correct voice interacting-command. Likewise, the intonation of syllables and/or words spoken as part of an erroneous voice interacting-command may be characterized by a decreased pitch as compared to syllables and/or words following a correct voice-interacting-command which is driven by a correct decision.

On the other hand, the intonation of syllables and/or words following an erroneous voice interacting-command may be characterized by an elevated pitch as compared to syllables and/or words following a correct voice-interacting-command which is driven by a correct decision.

Similarly, the voice intensity (amplitude) while uttering syllables and/or words following an erroneous voice interacting-command may be greater than the voice intensity (amplitude) of syllables and/or words following a correct voice-interacting-command driven by a correct decision. Alternatively, spoken syllables and/or words and/or vocal gestures comprising an erroneous voice command may be abruptly stopped before completion.

Furthermore, according to the presently disclosed subject matter, command related data indicating incorrect interaction-command and/or an incorrect interacting-action may further include sub-movements. It is assumed that at least in some scenarios, instead of applying continuous motor control to a movement (of a body part), the brain controls actions by initiating discrete sub-movements. These sub-movements allow the brain to correct errors in a movement as they unfold. Sub-movements can be observed in the movement velocity profile across time as a series of bell-shaped functions, each representing a sub-movement (see, Chang, Y. H., Chen, M., Gowda, S., Overduin, S., Carmena, J. M. & Tomlin, C. (2013, December). Low-rank representation of neural activity and detection of submovements. In *Decision and Control (CDC)*, 2013 *IEEE* 52nd *Annual Conference* on (pp. 2544-2549). IEEE, which is incorporated herein by reference in its entirety). Sub-movements can also be observed in EMG and EEG motor cortical activity profiles.

As is well known to any person who is skilled in the art, there are several ways to divide a movement into a primary movement (the complete movement comprising the sub-movements) and any sub-movement therein. One such way is calculating the third derivative of the position (jerk) and pinpointing zero crossings observed from movement initiation to movement termination. In an offline analysis, the total number of zero crossings can be divided by two in order to conclude the total number of movements (velocity peaks) in a given movement route. According to the presently disclosed subject matter, information indicative of sub-movements can be utilized (by system 110) for determining whether a respective command and/or action are erroneous or not.

Furthermore, according to the presently disclosed subject matter, command related data may further include activation of facial muscles. Differences between activation of facial muscles associated with an incorrect interacting-command and/or an incorrect interacting-action and correct interacting-commands and/or an incorrect interacting-action, may be based on activation of a single facial muscle or a group of muscles at a specific facial location (e.g., the eyes, the eyebrows, the frown line, the nose, the nasolabial folds, and the mouth) or based on combination of facial muscles activation at several facial locations. Variations in the activity of facial muscles indicating an incorrect interacting-command and/or an incorrect interacting-action may include increased activity at some muscles, reduced activity in other muscles or a combination of both.

During real-time interaction of a user with a monitored machine 109 command related data is determined (block 705) as well as the respective command related data patterns of the command related data (block 707). The determined patterns of real-time command related data are compared to command related patterns indicative of interaction-error for determining whether the command related data is indicative of an interaction-error occurring in real-time (block 709).

In addition, an interacting-command or interacting-action can be analyzed to determine whether it develops according to the expected pattern. The relative change in command related data parameters along an executed interacting-command or interacting action can be determined. Based on the known relative change in command related data, command related data values in a given instant along an interacting-command or interacting action can be predicted, based on command related data values measured in earlier instances along the same interacting-command or interacting action. A comparison between the predicted values and the actual values can serve to identify interaction-errors.

The following operations can be executed by unit 103 for detecting interaction-errors. During the execution of an interaction-command or interacting-action, a first command related data value at a first instant can be determined (measured). Based on the first command related data value, an expected command related data value at a later instant along the executed interacting-command or interacting action is estimated. The actual command related data value is measured when the later instant arrives. The measured command related data value and expected command related data value are compared. If the difference between the expected command related data value and the measured command related data value complies with a predefined criterion (e.g. is greater by a predefined value), an interaction-error is determined.

For example, an interacting-action can be analyzed to determine whether the respective muscle movement develops according to the expected pattern. The expected intensity (amplitude) or the intensity rate of the measured command related data parameters (e.g., EMG amplitude, movement velocity, force, pressure) at a given instance can be estimated based on the intensity measured in the preceding instant. If the motor reaction is interfered with (e.g. by a compensation process attempting to cancel or correct the action) along its way, the actual measured intensity (or respective rate) in a given instant would fail to meet the expected value based on the previous instant.

According to a different example, an interacting-action can be analyzed to determine whether the respective pupil dilation develops according to the expected pattern. The expected intensity (amplitude or size), or the dilation rate (i.e. the measured command related data) at a given instance, can be estimated based on the intensity measured in the preceding instant. According to this example, if pupil dilation is resulted by an error detection process, the actual measured intensity (or respective rate) in a given instant would be different than the value expected based on the previous instant.

According to another example, an increase in acceleration, which is recorded in an agonist muscle during a non-erroneous interacting-action, is expected to be accompanied by an increase in acceleration rate. However, if a motor interacting-action is an erroneous interacting-action, and hence interfered with by a compensation process, the acceleration development would no longer be accompanied by increased rate of acceleration or be accompanied by reduced increase in acceleration rate.

Information indicative of relative change in command related data parameters along an executed interacting-command or interacting action can be obtained for example by recording command related data during the interaction of a plurality of users, analyzing the command related data, identifying respective patterns and determining the expected relative change in command related data values along the interacting command or interacting-action.

According to further aspects of the presently disclosed subject matter in addition to the identification of interaction errors during the interaction of a user with a machine, command related reference data can be used for monitoring behavioral and operational patterns of a user and determining changes in such patterns and evaluating user performance.

As mentioned above, command related data values can be recorded during interaction of a user with a human-machine interaction device and used for calculating user-specific command related data statistics. Different types of command related data statistics can be calculated, each type representing a respective comparative command related reference data measured in specific circumstances and/or time.

As further mentioned above, command related data statistics representing the performance of a population of users (population specific) can be used as references for evaluating the performance of a specific user. Command related data collected during the interaction of a specific user with a given human-machine interaction device can be compared with the population command related data statistics to determine whether the user's reactions deviate from normal reactions in the tested population. This approach can assist in evaluating the performance of a user during interaction with a given machine. For example, reactions of drivers can be tested to help determine their driving skills. In an additional example, reactions of a user can be compared to normal command related data values for the purpose of identifying medical and/or cognitive deficiencies.

Furthermore, user-specific command related data statistics can be calculated based on command related data collected during the interaction of a user with a given human-machine interaction device over time. Once user-specific command related data statistics are determined, these can be compared with command related data of the same user collected during another period of time, or real-time interaction with the human-machine interaction device. This comparison can assist in identifying deviation of user performance from his/her normal performance. For example, command related data of a given user can be collected during different times during the day (e.g. morning, noon, afternoon, night) and compared with normal user-specific command related data statistics and used for determining whether the user's performance varies during different hours of the day.

Similarly, user's command related data recorded during various specific conditions can be compared to user-specific and/or population-specific command related data statistics in order to determine the performance of the user during these conditions. Such specific conditions can include for example, high/low temperature conditions, performance under stressful conditions, etc.

Command related data statistics can be collected and classified into specific categories each category representing command related data recorded under certain conditions. Categorization of command related data enables to analyze user performance under various specific conditions, and can further be used to create more relevant command related reference data.

User command related data can be monitored and compared to user-specific and/or population-specific command related data statistics for identifying improvement or deterioration in user performance. For example, the effect of a medication on the performance of a user can be determined by comparing command related data before and after commencement of a medication treatment.

Furthermore, additional conditions can be related to specific user activity which is being carried out concurrently with user machine-interaction. For example, a computerized device such as a cellular device can be configured to identify various types of user activities such as, walking, running, driving, speaking on the phone, etc. As explained above, the performance of the user during these conditions can be determined as well.

Similarly, the performance (e.g. cognitive performance) of a user or users while using different applications can also be determined in order to determine whether there is a difference in the user performance while interacting with different applications.

In order to evaluate user performance, interaction-error detection unit 103 can be configured to determine whether there is a difference in the occurrence of errors in various conditions as compared to predefined command related data statistics. Alternatively or additionally, in order to evaluate user performance, interaction-error detection unit 103 can be configured to identify deviations in the command related data during human-machine interaction based on comparison to command related data statistics, including data which is not necessarily indicative of interaction-errors.

In addition, interaction-error detection unit 103 can be configured to store in a data repository (313) data indicating the statistical distribution of interaction-errors made by a certain user while performing specific user activities. Interaction-error detection unit 103 can be further configured to receive information (e.g. from the monitored machine) indicative of a certain user activity which is being performed by the user (e.g. driving, walking, etc.) and use the stored statistical data for estimating a probability of occurrence of an interaction-error. Optionally, if the estimated probability is greater than a certain threshold, interaction-error detection unit 103 can be configured to warn the user prior to issuance of an interaction-alert, and thereby help to avoid the interaction-error before it occurs.

The following section includes a number of examples of systems implementing the principles of the presently disclosed subject matter. Any one of the following machines and devices can be configured with an interaction-error detection system 110 comprising an interaction-error detection unit 103 configured to detect interaction-errors made by an operator of the machine.

Heavy machinery such as trucks, tractors, excavators, buggers, etc. Interaction-error detection unit 103 can be operatively connected to the control interface and control circuitry configured for controlling an implement and to block operations initiated by erroneous interacting commands and/or erroneous interacting-actions of the operator while interacting with the implement control interface.

Head-mounted displays (such as Google glass and helmet mounted display) configured with one or more human-machine interaction devices such as: a touchpad or buttons, voice command interface, gesture recognition interface, eye tracking interface, etc.

Powered exoskeleton configured as a mobile machine consisting of a wearable outer framework with a powered system that delivers at least part of the energy for limb movement. Erroneous-command detection system 110 can be operatively connected to a control unit of the exoskeleton and configured to block or correct limb movement of the exoskeleton which is initiated by an erroneous interacting command and/or erroneous interacting-action. Alternatively, erroneous-command detection system 110 can update an adaptive decoding algorithm supporting the exoskeleton operation, so fewer errors will be made in future operations of the exoskeleton.

Neuroprosthetics—Bionic limbs can comprise or be operatively connected to erroneous-command detection system 110 configured to block or correct limb movement of the limb which is initiated by an erroneous interacting command and/or erroneous interacting-action. Alternatively, erroneous-command detection system 110 can update an adaptive decoding algorithm supporting the bionic limb operation, so fewer errors will be made in future operations of the bionic limb.

Robotic surgical system (e.g. da Vinci Surgical System) can comprise or be operatively connected to erroneous-command detection system 110 configured to block or correct movements of the surgical arms which are initiated by an erroneous interacting command and/or erroneous interacting-action. Alternatively, erroneous-command detection system 110 can update an adaptive decoding algorithm supporting the robotic surgical system operation, so fewer errors will be made in future operations of the robotic surgical system.

Biofeedback (or Neurofeedback) is a technique aimed at learning to control physiological and brain functions through immediate performance feedback. Humans lack conscious access to self performance monitoring mechanisms (i.e., brain mechanisms monitoring the execution of decisions and actions and alerting unexpected outcomes), governing interaction-error detection and/or compensation. However, these mechanisms are constantly active, affecting an interaction error in various degrees, e.g. from slowing down an erroneous action to having it stopped completely. Performance monitoring mechanisms may be also responsible for the initiation of swift and accurate correction of an interaction error. Bringing the activity of performance monitoring to a person's attention can serve as performance feedback.

Feedback is expected to reinforce the performance monitoring mechanisms by providing information indicative of what is an efficient performance monitoring mechanism, and how is it different from inefficient performance monitoring mechanisms. Efficiency of performance monitoring mechanisms can be determined based on various command related data parameters. For example, the speed of detecting an erroneous action (e.g. the time elapsing from the initial action to the time an erroneous action has been detected) and/or the magnitude of the difference between the measured command related data parameters when an interaction error is detected, as compared to the value which is detected during a correct interaction.

According to Biofeedback/Neurofeedback principles, repeating this procedure many times in an environment that induces many errors has the potential of teaching a person to consciously control and/or improve his/her performance monitoring mechanisms. Alternatively or additionally, the performance monitoring mechanisms may be directly affected (unconsciously) by this procedure.

Feedback may include for instance, alerting the occurrence of an error, correcting the error, or preventing the error altogether. Prevention of an error can be facilitated by stopping the action of the user (e.g. by exerting a counter force as exemplified below) and/or by stopping or changing the result of the action (e.g. changing the data which is displayed responsive to the action).

Feedback may include a counter-reaction generated for preventing the error from occurring. For example, exerting a counter force contradicting the force exerted by the erroneous action. In a more specific example this may be the case in a task involving moving either of two joysticks (or levers) where an operator is required to choose at a given moment which of the joysticks should be moved. The generated feedback may include exerting a counter force on a joystick capable of stopping an erroneous attempt of the operator to move the wrong joystick.

According to some examples, the generated feedback can be proportional to the measured command related data parameters of the error detection/compensation process. For example, the time from the initial movement of a body part interacting with a human-machine interacting device to the time where an erroneous action is initially detected can be measured, and, based on the elapsed time, a respective feedback can be generated. According to some examples, the shorter the elapsed time, the stronger the feedback provided to the operator. This enables to provide to the operator an indication of the efficiency of the operator's performance monitoring.

Furthermore, as mentioned above, it is assumed that at least in some scenarios, during execution of a movement, the movement is divided by the brain into discrete sub-movements. These sub-movements may be indicative of an incorrect or inaccurate execution of the desired movement. A person initiating the movement is usually unaware of both the error in the movement or any attempts of the brain to prevent or correct the error. According to the presently disclosed subject matter, Biofeedback/Neurofeedback can include feedback indicating the occurrence of corrective sub-movements. Making a person aware of corrective sub-movements through feedback as they unfold (feedback may be proportional to the efficiency of the corrective measures), may reinforce a person's learning as how to consciously control his/her performance monitoring mechanisms. Alternatively or additionally, the performance monitoring mechanisms may be directly affected (unconsciously) by the procedure.

Thus, the presently disclosed subject matter further contemplates a biofeedback/Neurofeedback device aimed at training a person's performance monitoring mechanisms, comprising or otherwise operatively connected to interaction-error detection system 110 and configured to provide biofeedback (e.g. alert, reverse, block, slowdown or correct movements initiated by an erroneous interacting command and/or erroneous interacting-action). For example, if a person is using a joystick to control a cursor, upon error detection the biofeedback device can be configured, responsive to receiving an indication of an interaction error, to momentarily freeze the joystick or exert counter-force on the joystick to prevent the erring operator/user from moving the joystick any further. The biofeedback device can be further configured to repeatedly provide biofeedback to the person in order to reinforce successful error detection and compensation. According to some examples, preventive action initiation module 307 in interaction error detection unit 103 can be configured for providing biofeedback.

According to the presently disclosed subject matter, the proposed biofeedback mechanism and method can be harnessed for assisting in the rehabilitation of people suffering, for example, from brain damage, dementia, mental illness, personality disorders and/or motor disabilities. For example, it can be used to train a person's performance monitoring mechanisms to efficiently detect and prevent mental and/or behavioral irregularities. In people suffering from motor disabilities due to inability to learn from what is known to those skilled in the art as "sensory prediction errors", the proposed Biofeedback may be used to train motor learning through an alternative mechanism, known to those skilled in the art as learning from reward prediction errors.

An example of a Biofeedback procedure aimed at training motor learning from reward prediction errors is described herein. A user is tracking a moving target on a computer screen by using a joystick to control a cursor. Occasionally the joystick exerts a counter force or reduces resistance to the user's own force, interfering with joystick/cursor manipulation by the user. In order to continue with the planned movement, the user must initiate compensatory maneuvers such as initiating sub-movement or reducing his own force exerted on the joystick. At the beginning of training, joystick counter force or reduced resistances are of large magnitude, so the user is aware of both the changes to joystick counterforce or reduced joystick resistance and his resulting own compensatory reactions. However, during training, joystick counterforce and/or reduced resistance gradually become more subtle. As a result, a user's compensatory reactions also become more subtle, so the user is no longer aware of both joystick counterforce and/or reduced resistance and resulting compensatory reactions, especially if the user's own compensatory reactions are not efficient enough to affect the ongoing movement. Here, a feedback is given to a user whenever interaction-error detection system 110 identifies activation of user's performance monitoring. The feedback is expected to reinforce the activation of a user's performance monitoring mechanisms.

As is well known in the art, increased reaction time of person to a stimulus may possibly be related to development of various chronic diseases and higher risk of mortality. Thus, the time it takes a person to detect or compensate for an error, may be indicative of certain aspects of the person's health status. According to the presently disclosed subject matter, interaction-error detection system 110 can be configured to compute the time from the occurrence of stimuli prompting the erroneous action or occurrence of environmental changes rendering an action incorrect, or the time from erroneous action initiation, to the time of error detection or compensation or any error detection-related actions. Alternatively, interaction-error detection system 110 can be configured to compute the time from error detection or compensation to any error-detection related actions. Collected data can then be compared against population norms or the person's own previously collected data, and used for detection of possible health problems.

A steering wheel or any other type of vehicle control and maneuvering device can comprise or be operatively connected to erroneous-command detection system 110 configured to override steering and/or control commands which are initiated by erroneous interacting command and/or erroneous interacting-action.

Standard car pedals can comprise or be operatively connected to erroneous-command detection system 110 configured to override a resulting system operation (e.g. fuel delivery to the engine or breaking) generated by the pedal in case an erroneous interacting command and/or erroneous interacting-action is identified. The pedal can be equipped with an appropriate sensor such as a strain gauge located underneath the pedal. The examples described hereinabove are provided in order to illustrate possible implementations of the disclosed subject matter and should not be construed as limiting in any way. Any additional systems configured according to similar principles are considered within the scope of the presently disclosed subject matter.

It is to be understood that the presently disclosed subject matter is not limited in its application to the details set forth in the description contained herein or illustrated in the drawings. The presently disclosed subject matter is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the present presently disclosed subject matter.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

While various embodiments have been shown and described, it will be understood that there is no intent to limit the invention by such disclosure, but rather, it is intended to cover all modifications and alternate constructions falling within the scope of the invention, as defined in the appended claims.

The invention claimed is:

1. A human-machine interface system configured and operable to control machine operation of a machine via monitoring cognitive brain commands of a user while under human-machine interaction condition with respect to the machine, wherein the human-machine interface system comprises:
    at least one sensor configured for operative connection to at least one body part of the user and generate sensing data comprising data indicative of the cognitive brain commands of the user in association with the machine operation, and
    a computer processor configured for data communication with said at least one sensor, the computer processor being adapted to process said sensing data to identify, in said data indicative of the cognitive brain commands of the user, motor-command related data indicative of motor commands controlling user interaction with the machine and store the motor-command related data in a memory, wherein the computer processor comprises an error detector configured and operable to analyze data indicative of the motor-command related data and determine a relation of said motor-command related data to command related reference data, and upon identifying, based on the determined relation, that the motor-command related data corresponds to a condition of user's detection of error in the cognitive brain command of the user, generate and store in the memory the motor-command related data indicative of said condition of user's detection of error, thereby enabling to carry out at least one of the following: (i) selectively utilize said stored motor-command related data to enhance said command related reference data; and (ii) issue an alert data indicative of said condition of user's detection of error.

2. The human-machine interface system according to claim 1, wherein said condition of user's detection of error in the cognitive brain command of the user is indicative of user's predicted error.

3. The human-machine interface system according to claim 1, wherein said error detector is configured and operable to determine whether the identified data indicative of the motor-command related data corresponds to an erroneous-command data or not, and upon identifying the erroneous-command data categorizing the respective motor-command related data as the erroneous-command data and storing it in association with a corresponding human-machine interaction condition of.

4. The human-machine interface system according to claim 1, wherein said computer processor is adapted to identify, in the motor-command related data, the motor-commands corresponding to cognitive commands indicative of user's intention to generate a specific machine operation.

5. The human-machine interface system according to claim 1, characterized by at least one of the following: (1) said human-machine interaction condition corresponds to user's interaction with the machine having a direct effect on the machine operation; and (2) said human-machine interaction condition corresponds to user's observation of the machine operation.

6. The human-machine interface system according to claim 1, wherein the computer processor is configured and operable to carry out at least one of the following: (1) utilize the stored motor-command related data to enhance the command related reference data indicative of the condition of user's detection of error in the cognitive brain command of the user; (2) perform corroboration of the command related reference data; and (3) analyze the motor-command related data, and, upon identifying that said motor-command related data corresponds to a condition of a correct interacting-action, storing the respective motor-command related data as characterizing the correct interaction-action, to thereby enhance the command related reference data corresponding to the correct interacting-action condition.

7. The human-machine interface system according to claim 1, wherein the computer processor is further configured and operable to perform corroboration of the command related reference data by identifying user's input data indicative of correction of an actual interaction error, and categorizing the respective stored motor-command related data as relating to an erroneous interaction-error.

8. The human-machine interface system according to claim 1, wherein the computer processor is further configured and operable to analyze the motor-command related data, and, upon identifying that said motor-command related data corresponds to a condition of a correct interacting-action, storing the respective motor-command related data as characterizing the correct interaction-action, to thereby enhance the command related reference data corresponding to the correct interacting-action condition.

9. The human-machine interface system according to claim 1, comprising a human-machine interaction device operatively connected to the machine and configured to input data to cause a direct effect on the machine operation, thereby enabling the user's interaction with the machine.

10. The human-machine interface system according to claim 9, wherein said error detector comprises a command related data acquisition module configured and operable to obtain the motor-command related data recorded by the computer processor during interaction of the user with the human-machine interacting device.

11. The human-machine interface system according to claim 1, wherein said at least one sensor, adapted to generate the sensing data comprising data indicative of the cognitive brain commands of the user, is configured for operative connection to at least one of the following: operative connection to at least one part of user's body other than user's brain; and operative connection to user's brain.

12. The human-machine interface system according to claim 1, wherein said at least one sensor is configured for operative connection to at least one part of user's body other than user's brain for measuring one or more of the following: measuring electromyography (EMG) at a muscle of said at least one part of the user's body; measuring kinematics at said at least one part of the user's body; measuring autonomic nervous system reaction data related to user's motor activity; and an increase and/or decrease in activity rate of motor neurons.

13. The human-machine interface system according to claim 1, wherein said at least one sensor is configured and operable for measuring command related data derived from and characterizing a motor-command generated by the user, while under the human-machine interaction condition with respect to the machine, for instructing a body part of the user other than user's brain interacting with the machine to perform an interacting-action for the purpose of interacting with the machine.

14. The human-machine interface system according to claim 13, wherein said at least one sensor is configured and operable for measuring, at said human-machine interaction device operatively connected to the machine, command related data derived from and characterizing a motor-command generated by the user, while under the human-machine interaction condition, for instructing a body part of the user other than user's brain interacting with the machine to perform an interacting-action for the purpose of interacting with the machine, measured command related data comprising one or more of the following: kinematics resulting from the interacting-action; force, or derivative thereof, applied on the human-machine interaction device resulting from the interacting-action; time to lift of the at least one body part from the human-machine interaction device.

15. The human-machine interface system according to claim 13, wherein the interacting-action is a voice command, said at least one sensor being configured and operable for measuring the command related data relating to changes in activity of muscles related to speech.

16. The human-machine interface system according to claim 13, wherein said at least one sensor is configured and operable for measuring patterns representing variation in the command related data measured along progression of at least one of the motor-command and the interacting-action.

17. The human-machine interface system according to claim 13, wherein said computer processor is configured and operable for determining from the sensing data a first command related data value at a first instant along an executed interacting-action; based on the first command related data value, estimating an expected command related data value at a later instant along the executed interacting action; the expected command related data value serving as the command related reference data values; determining from the sensing data a second command related data value at the later instant; and determining that an interaction-error occurred during the interaction of the user with the machine, if a difference between the expected command related data value and the second command related data value complies with certain criterion.

18. The human-machine interface system according to claim 1, wherein said error detector comprises at least one of the following: (a) an interaction-error determination module configured to determine the relation of said motor-command related data to the command related reference data indicative of the condition of user's detection of error in the cognitive brain command of the user; and (b) a preventive action initiating module configured to initiate one or more prevention actions in response to detection of the motor-command relating data corresponding to an erroneous-command, said one or more preventative actions comprising instructions for one or more of the following: delaying execution of the erroneous-command, aborting execution of the erroneous-command, undoing execution of the erroneous-command, and replacing an outcome of the erroneous-command.

19. A human-machine interface system configured and operable to control an operation of a machine via monitoring cognitive brain commands of a user while under human-machine interaction condition with respect to the machine, wherein the human-machine interface system comprises:
  at least one sensor configured for operative connection to at least one body part of the user and generate sensing data comprising data indicative of the cognitive brain commands of the user in association with the operation of the machine, and
  a computer processor configured for data communication with said at least one sensor, the computer processor being adapted to process said sensing data to identify, in said data indicative of the cognitive brain commands of the user, motor-command related data indicative of motor commands controlling user interaction with the machine and store the motor-command related data in a memory, wherein the computer processor comprises an error detector configured and operable to analyze the motor-command related data and determine a relation of said motor-command related data to command related reference data, and upon identifying, based on the determined relation, that the motor-command related data corresponds to a condition of user's detection of error in the cognitive brain command of the user, categorizing the motor-command related data as an erroneous-command data, and generating and storing said erroneous-command data in association with the condition of user's detection of error, thereby enabling to carry out at least one of the following: (i) selectively utilize said motor-command related data comprising said erroneous-command data to enhance said command related reference data; and (ii) issue an alert data indicative of said erroneous-command data.

20. A method of controlling an operation of a machine via monitoring cognitive brain commands of a user while under human-machine interaction condition with respect to the machine, the method comprising:
  providing sensing data measured by at least one sensor operatively connected to at least one body part of the user while under said human-machine interaction condition and comprising data indicative of user's cognitive brain commands in association with the operation of the machine, and
  processing said sensing data to detect an interaction-error condition, said processing comprising:
    identifying, in said data indicative of the user's cognitive brain commands, motor-command related data indicative of motor commands controlling user interaction with the machine,
    analyzing the motor-command related data and determining a relation of said motor-command related data to command related reference data, and upon identifying, based on the determined relation, that the motor-command related data corresponds to a condition of user's detection of error in the user's cognitive brain command, generating and storing the motor-command related data in association with said condition of user's detection of error, thereby enabling to carry out at least one of the following: (i) selectively utilize the motor-command related data to enhance said command related reference data; and (ii) issue an alert data indicative of user's detection of error.

21. A non-transitory program storage device readable by a computer, tangibly embodying a program of instructions executable by the computer to perform a method of detecting an interaction-error condition during user's interaction with a machine, the method comprising: processing sensing data, provided by at least one sensor operatively connected to at least one body part of the user during the user's interaction and comprising data indicative of cognitive brain commands of the user, said processing comprising identifying, in said data indicative of the cognitive brain commands of the user, motor-command related data indicative of motor commands controlling the user's interaction with the machine and storing the motor-command related data in a memory; determining a relation of said motor-command related data to command related reference data; and upon identifying, based on the determined relation, that the motor-command related data corresponds to a condition of user's detection of error in the cognitive brain command of the user, generating and storing the motor-command related data indicative of said condition, thereby enabling to carry out at least one of the following: (i) selectively utilize the stored motor-command related data to enhance said command related reference data; and (ii) issue an alert data indicative of said condition of user's detection of error.

* * * * *